US011292779B1

(12) United States Patent
Olson et al.

(10) Patent No.: US 11,292,779 B1
(45) Date of Patent: Apr. 5, 2022

(54) PROCESS FOR PRODUCTION OF ESSENTIALLY PURE Δ8-TETRAHYDROCANNABINOL FROM CANNABIDIOL EXTRACTED FROM HEMP

(71) Applicant: CCT SCIENCES, LLC, Clearwater, FL (US)

(72) Inventors: Kyle Olson, Clearwater, FL (US); Mario Tremblay, Clearwater, FL (US)

(73) Assignee: CCT SCIENCES, LLC, Clearwater, FL (US)

( * ) Notice: Subject to any disclaimer, the term of this patent is extended or adjusted under 35 U.S.C. 154(b) by 0 days.

(21) Appl. No.: 17/214,229

(22) Filed: Mar. 26, 2021

(51) Int. Cl.
| | |
|---|---|
| C07D 311/80 | (2006.01) |
| A61K 9/00 | (2006.01) |
| B01D 3/10 | (2006.01) |
| B01D 1/22 | (2006.01) |
| B01D 5/00 | (2006.01) |
| A23L 33/105 | (2016.01) |
| B01D 1/08 | (2006.01) |
| C07B 37/10 | (2006.01) |
| C07B 63/02 | (2006.01) |
| C07B 63/04 | (2006.01) |
| C07B 37/08 | (2006.01) |
| C07B 41/06 | (2006.01) |
| C07B 41/04 | (2006.01) |
| C07C 39/23 | (2006.01) |

(52) U.S. Cl.
CPC .......... *C07D 311/80* (2013.01); *A23L 33/105* (2016.08); *A61K 9/0014* (2013.01); *A61K 9/0056* (2013.01); *B01D 1/08* (2013.01); *B01D 1/22* (2013.01); *B01D 3/10* (2013.01); *B01D 5/0063* (2013.01); *C07B 37/08* (2013.01); *C07B 37/10* (2013.01); *C07B 41/04* (2013.01); *C07B 41/06* (2013.01); *C07B 63/02* (2013.01); *C07B 63/04* (2013.01); *A23V 2002/00* (2013.01); *C07B 2200/09* (2013.01); *C07C 39/23* (2013.01)

(58) Field of Classification Search
CPC ....... C07D 311/80; C07B 41/04; C07B 41/06; C07B 37/08; C07B 63/04; C07B 37/10; C07B 63/02; C07B 2200/09; B01D 1/08; B01D 3/10; B01D 1/22; B01D 5/0063; A23L 33/105; A61K 9/0014; A61K 9/0056; C07C 39/23; A23V 2002/00
USPC ........................................................ 514/454
See application file for complete search history.

(56) References Cited

U.S. PATENT DOCUMENTS

2008/0221339 A1 * 9/2008 Webster ............... C07D 311/80
549/390

OTHER PUBLICATIONS

Wikipedia , Distillation, Feb. 24, 2020, p. 1-16. (Year: 2020).*

* cited by examiner

*Primary Examiner* — Taylor V Oh
(74) *Attorney, Agent, or Firm* — Juneau & Mitchell; Todd L. Juneau

(57) ABSTRACT

The present invention describes a process to isomerize industrial hemp derived Cannabidiol (CBD) to a pure Δ8-tetrahydrocannabinol (Δ8-THC) extract. This procedure will produce Δ8-tetrahydrocannabinol that is essentially free from any detectable levels of Δ9-tetrahydrocannabinol (Δ9-THC). Included in this filing are methods and processes to scale the reaction from the lab to process to large scale manufacturing. Additionally, the resulting extract from said methods and processes consists of higher purity than previously reported in the art and greater efficiency compared to prior art.

16 Claims, 7 Drawing Sheets

FIGURE 2 - Process

FIGURE 5

(i) refluxing a cannabidiol extract from industrial hemp having less than 0.3% Δ9-THC in a mixture of toluene and p-toluenesulfonic acid monohydrate at about 70°C-100°C for about 120-1440 minutes to obtain a reaction mixture having less than 0.3% Δ9-THC;

(ii) verifying the reaction mixture compliance of less than 0.3% Δ9-THC using a verification method selected from the group consisting of post decarboxylation, HPLC, GC, GC-MS, GC-FID, HPLC-MS, HPLC-UV, HPLC-DAD, HPLC-ESI-qTOF, HPLC-MS/MS, UPLC, UPLC-qTOF, MALDI-MS, TLC, FTIR, and NMR.

(iii) adding aqueous sodium bicarbonate to neutralize the reaction mixture, adding water, and evaporating to obtain a crude Δ8-THC oil having about 73.59-99.73% Δ8-THC by HPLC and less than 0.3% Δ9-THC by HPLC; and (iv) verifying the crude Δ8-THC oil compliance of less than 0.3% Δ9-THC using a verification method selected from the group consisting of post decarboxylation, HPLC, GC, GC-MS, GC-FID, HPLC-MS, HPLC-UV, HPLC-DAD, HPLC-ESI-qTOF, HPLC-MS/MS, UPLC, UPLC-qTOF, MALDI-MS, TLC, FTIR, and NMR.

FIGURE 6

(i) refluxing a cannabidiol extract 23% wt/wt from industrial hemp having less than 0.3% Δ9-THC in a mixture of toluene and p-toluenesulfonic acid monohydrate 0.12%-0.598% (w/w) at about 70°C-100°C for about 120-1440 minutes to obtain a reaction mixture having less than 0.3% Δ9-THC;
(ii) verifying the reaction mixture compliance of less than 0.3% Δ9-THC using post decarboxylation and/or high performance liquid chromatography (HPLC);

(iii) adding aqueous sodium bicarbonate (10% NaHCO3) to neutralize the reaction mixture, adding water, and evaporating to obtain a crude Δ8-THC oil having about 73.59-99.73% Δ8-THC by HPLC and less than 0.3% Δ9-THC by HPLC;
(iv) verifying the crude Δ8-THC oil compliance of less than 0.3% Δ9-THC using post decarboxylation and/or HPLC;

(v) Vacuum distilling the crude Δ8-THC oil with a short path vacuum distillation system until a clear Δ8-THC distillate starts to condense and then immediately stopping the vacuum distilling, wherein said vacuum distilling removes residual solvent and volatile cannabidiol impurities from the clear Δ8-THC distillate;
(vi) Wiped film distilling the clear Δ8-THC distillate with a wiped film distillation unit to obtain a Δ8-THC oil having >99% Δ8-THC by HPLC, wherein said wiped film distilling removes high temperature cannabinoid impurities having a non-vacuum boiling higher than 180°C.;
(vii) verifying the clear Δ8-THC distillate and/or the Δ8-THC oil compliance of less than 0.3% Δ9-THC using post decarboxylation and/or HPLC; and
(viii) optionally performing step (vi) a second time.

PROCESS FOR PRODUCTION OF ESSENTIALLY PURE Δ8-TETRAHYDROCANNABINOL FROM CANNABIDIOL EXTRACTED FROM HEMP

FIELD OF THE INVENTION

The invention relates to the field of cannabinoid synthesis, and in particular the chemical processes for making Δ8-tetrahydrocannabinol from cannabidiol extract of industrial hemp having less than 0.3% Δ9-tetrahydrocannabinol using processes that do not permit isomerization of cannabidiol to Δ9-tetrahydrocannabinol to maintain compliance with federal laws throughout processing, and using a differential distillation using vacuum distillation for volatile or low temperature impurities and wipe film distillation to remove high temperature impurities.

BACKGROUND OF THE INVENTION

Cannabinoids are an important class of diverse compounds that connect with brain receptors which are part of the endocannabinoid system. This series of receptors modulates homeostasis throughout the various facets of the human body. The most well-known receptors are the CB1 and CB2 that interact with the central nervous system and immune system respectively. There are over 100 naturally occurring cannabinoids with each affecting the body in specific ways and helping to alleviate a variety of conditions. The cannabinoid discussed in this application, Δ8-tetrahydrocannabinol, has shown great promise in promoting a general state of well-being in the user. According to The National Cancer Institute, Δ8-tetrahydrocannabinol is defined as "an analogue of Δ9-tetrahydrocannabinol with antiemetic, anxiolytic, appetite-stimulating, analgesic and neuroprotective properties."

Δ8-tetrahydrocannabinol has a lower psychotropic potency than Δ9-tetrahydrocannabinol which may further aid in its acceptance as a medicinal based cannabinoid. Additionally, Δ8-tetrahydrocannabinol binds to both the CB1 and CB2 receptors. CB1 receptors are found in the central nervous system, mainly in the spinal cord and brain. CB2 receptors are found on cells primarily associated with the immune system and are more broadly distributed, therefore influencing most of the body. Since Δ9-tetrahydrocannabinol predominantly interacts with the CB1 receptor, it has a more limited medicinal spectrum than that of Δ8-tetrahydrocannabinol. Lastly, Δ8-tetrahydrocannabinol has shown a reduction of side effects compared to Δ9-tetrahydrocannabinol with patients reporting much less paranoia and lethargy from its use.

Webster, Sarna, and Mechoulam (U.S. Pat. No. 7,399,872) describe a method for producing Δ8-tetrahydrocannabinol where they achieved an 81% yield of 86% Δ8-tetrahydrocannabinol as detected by High Performance Liquid Chromatography (HPLC). This method produces small amounts of Δ9-tetrahydrocannabinol which means that further purification by liquid chromatography is necessary to obtain a purified Δ8-tetrahydrocannabinol product. Our method improves quite significantly on the overall purity and yield of the Δ8-tetrahydrocannabinol in a single step reaction. Mechoulam and Abrahamov (U.S. Pat. No. 5,605,928) also details Δ8-tetrahydrocannabinol's antiemetic effects on children. Eight children were given a dose of Δ8-tetrahydrocannabinol before chemotherapy treatment and it was shown to effectively eliminate all vomiting with little to no side effects. Δ8-tetrahydrocannabinol has been shown to be 200% more effective as an anti-emetic than Δ9-tetrahydrocannabinol and has been especially helpful when used as an anti-emetic in children. (Abrahamov et al, 1995, Life Sciences 56: 2097-2102).

The Farm Bill of 2018 gave farmers in the United States the opportunity to grow industrial hemp on a nationwide basis. Due to many of the cultivars being high in Cannabidiol, there was major interest in cultivation for biopharmaceutical applications. After harvest, industrial hemp is typically processed using solvent such as ethanol, carbon dioxide, or hydrocarbon extraction to create a full spectrum extract. Further purification occurs through distillation and isolation of the Cannabidiol to increase potency and purity of the end product. The Farm Bill of 2018 states that hemp is defined as "the plant *Cannabis sativa* L." and any part of that plant, including the seeds thereof and all derivatives, extracts, cannabinoids, isomers, acids, salts, and salts of isomers, whether growing or not, with a delta-9 tetrahydrocannabinol concentration of not more than 0.3 percent on a dry weight basis." Given the large supply of industrial hemp and Cannabidiol in the United States, there exists a need to work towards using this cannabinoid more widely to produce other medicinally beneficial compliant compounds.

SUMMARY OF THE INVENTION

The inventive process starts with an industrial hemp plant that is less than 0.3% Δ9-THC. The cannabidiol (CBD) extract obtained from the compliant (verified less than 0.3% Δ9-THC) hemp is processed to also have less than 0.3% Δ9-THC. The next step of processing with an organic acid, e.g. p-toluenesulfonic acid, in a chemically-related and compatible solvent, e.g. toluene, followed by quenching with a weak base, e.g. sodium bicarbonate, and washing with water, also yields a crude Δ8-THC oil having less than 0.3% Δ9-THC. Thus, the entire Δ8-THC process stays Δ9-THC-compliant at each step. Further performing a short-path vacuum distillation to remove the low temperature impurities ensures that the crude Δ8-THC oil produces a Δ8-THC distillate without allowing cannabidiol to isomerize to the unwanted and non-compliant Δ9-THC. Lastly, performing a wiped film distillation to remove the high temperature impurities also ensures that the Δ8-THC distillate produces a highly pure Δ8-THC oil having >99% Δ8-THC by HPLC without allowing any further isomerization to the unwanted and non-compliant Δ9-THC.

The invention also includes compositions and formulations containing the Δ8-THC oil having >99% Δ8-THC by HPLC.

BRIEF DESCRIPTION OF THE FIGURES

FIG. 5 is a process flowchart showing yet another preferred embodiment of the inventive process described and claimed herein for obtaining a crude Δ8-THC oil having about 73.59-99.73% Δ8-THC by HPLC and less than 0.3% Δ9-THC by HPLC, and verifying the crude Δ8-THC oil compliance of less than 0.3% Δ9-THC using post decarboxylation and/or HPLC.

FIG. 6 is a process flowchart showing another preferred embodiment of the inventive process described and claimed herein for obtaining a crude Δ8-THC oil having about 73.59-99.73% Δ8-THC by HPLC and less than 0.3% Δ9-THC by HPLC, verifying the crude Δ8-THC oil compliance of less than 0.3% Δ9-THC using post decarboxylation and/or HPLC, then performing vacuum distillation of the crude Δ8-THC oil with a short path vacuum distillation system to obtain a clear Δ8-THC distillate, followed by a wiped film distillation of the clear Δ8-THC distillate to obtain a Δ8-THC oil having >99% Δ8-THC by HPLC, verifying the clear Δ8-THC distillate and/or Δ8-THC oil compliance of less than 0.3% Δ9-THC using post decarboxylation and/or HPLC, optionally followed by repeating the wiped film distillation a second time.

DETAILED DESCRIPTION OF THE INVENTION

The invention relates to the field of cannabinoid synthesis. More specifically, the process described covers industrial scale isomerization of Cannabidiol (CBD) into an essentially pure Δ8-tetrahydrocannabinol (Δ8-THC) extract. The chemical processes herein provides for making Δ8-tetrahydrocannabinol from cannabidiol extract of industrial hemp having less than 0.3% Δ9-tetrahydrocannabinol using processes for obtaining Δ8-THC that do not permit isomerization of cannabidiol to Δ9-tetrahydrocannabinol to maintain compliance with federal laws throughout processing, and using a differential distillation using vacuum distillation for volatile or low temperature impurities and wipe film distillation to remove high temperature impurities.

Essentially pure is defined as greater than 99% presence of Δ8-tetrahydrocannabinol on a weight to weight basis as detected by HPLC. Such purity of Δ8-tetrahydrocannabinol is generally accepted as a pharmaceutical, nutraceutical, skin care and/or cosmetic compositions. Additionally, the method consists of the ability not only to produce high purity Δ8-tetrahydrocannabinol (i.e. 90% to 99.9%) but also to scale up from converting hundreds of grams of CBD to the ability to convert hundreds of kilograms of CBD while maintaining said high Δ8-tetrahydrocannabinol (i.e. 90% to 99.9%). In essence the purity of said Δ8-tetrahydrocannabinol is considered essentially pure (i.e. 90% to 99.9%) on a weight to weight percent basis of the total composition.

Stated herein are the preferred and alternative methods for converting CBD to Δ8-THC. The reaction mixture can be manipulated by time, temperature, and catalyst concentration to produce extracts at different purities depending on the goal of the reaction.

Provided herein is a method of converting CBD to an essentially pure Δ8-THC with potency greater than 99%. This process is completed by introducing Cannabidiol from industrial hemp and adding it to a specific organic solvent with a specific catalyst to form a reaction mixture, loading the mixture into a reaction vessel, heating the solution to the preferred temperature, allowing it to reflux for the preferred duration, quenching the reaction mixture when complete, removing the aqueous phase, recovering the solvent, stripping the terpenes and distilling the crude residue to form a pure Δ8-THC extract.

PREFERRED EMBODIMENTS

Figure 2:
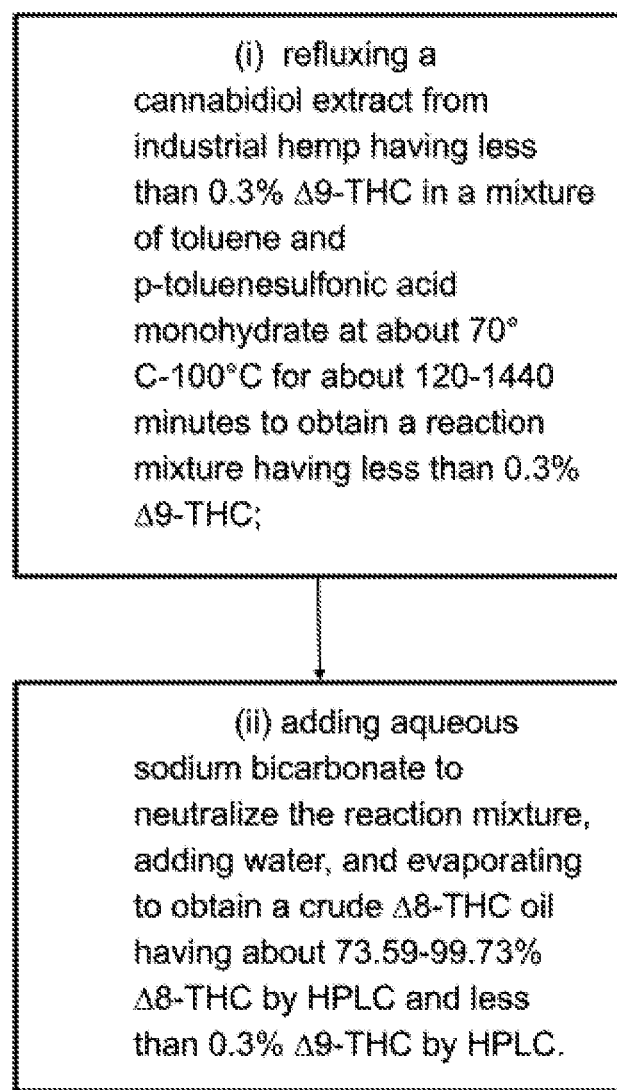
FIG. 2 is a process flowchart showing one preferred embodiment of the inventive process described and claimed herein for obtaining a crude Δ8-THC oil having about 73.59-99.73% Δ8-THC by HPLC and less than 0.3% Δ9-THC by HPLC.

In a preferred embodiment, as shown in FIG. 2, the invention relates to a process, having the steps of:

(i) refluxing a cannabidiol extract from industrial hemp having less than 0.3% Δ9-THC in a mixture of toluene and p-toluenesulfonic acid at about 70° C.-100° C. for about 120-1440 minutes to obtain a reaction mixture having less than 0.3% Δ9-THC; and (ii) adding aqueous sodium bicarbonate to neutralize the reaction mixture, adding water, and evaporating to obtain a crude Δ8-THC oil having about 73.59-99.73% Δ8-THC by HPLC and less than 0.3% Δ9-THC by HPLC.

Figure 3:
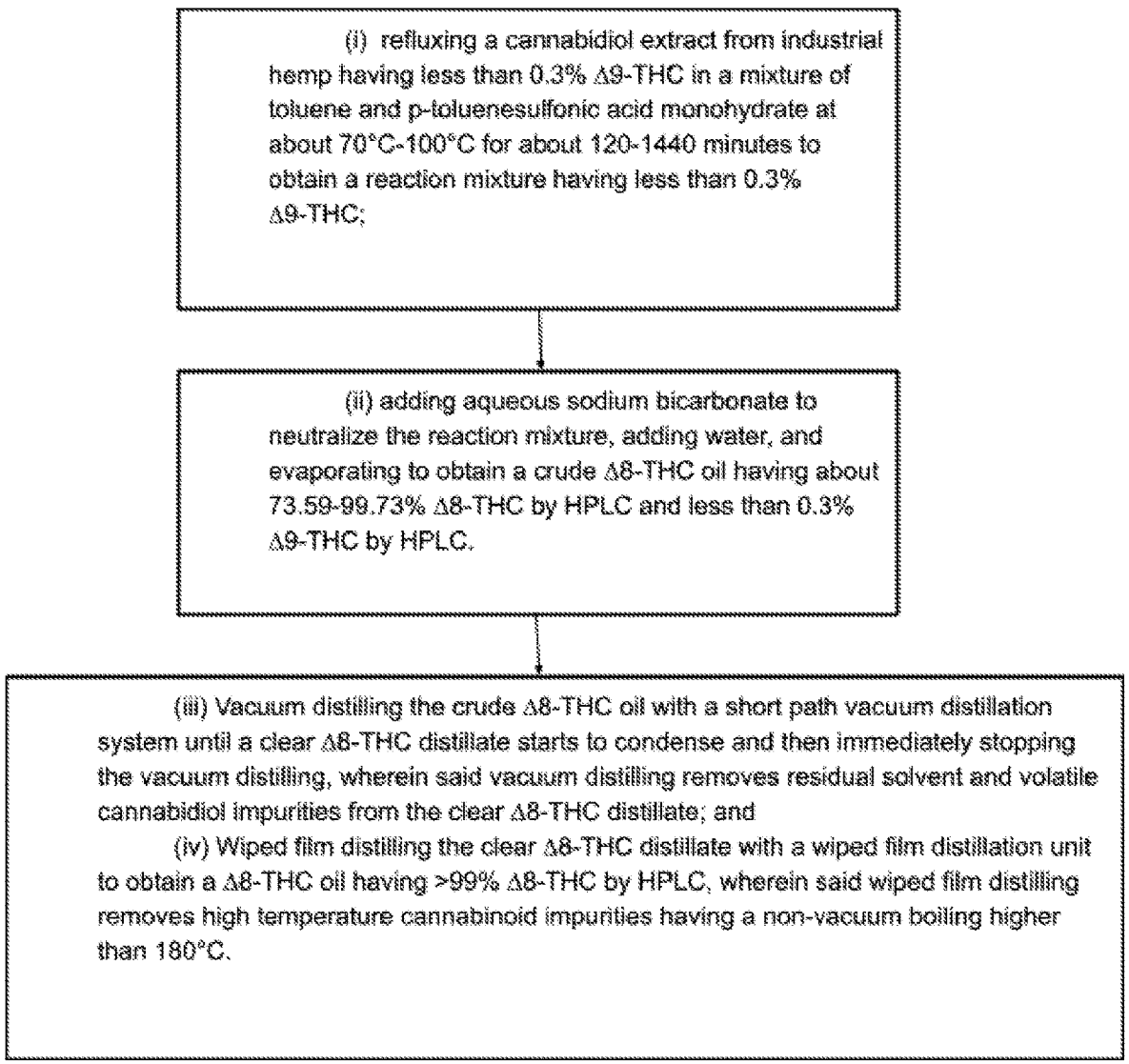
FIG. 3 is a process flowchart showing another preferred embodiment of the inventive process described and claimed herein for obtaining a crude Δ8-THC oil having about 73.59-99.73% Δ8-THC by HPLC and less than 0.3% Δ9-THC by HPLC and then performing vacuum distillation of the crude Δ8-THC oil with a short path vacuum distillation system to obtain a clear Δ8-THC distillate, followed by a wiped film distillation of the clear Δ8-THC distillate to obtain a Δ8-THC oil having >99% Δ8-THC by HPLC.

In another preferred embodiment, as shown in FIG. 3, the invention provides a process as described wherein the p-toluenesulfonic acid is about 0.12-0.598% (w/w) and the cannabidiol extract starting material is about 23% (wt/wt).

In another preferred embodiment, as shown in FIG. 3, the invention provides a process as described, comprising the additional steps of:

(iii) Vacuum distilling the crude Δ8-THC oil with a short path vacuum distillation system until a clear Δ8-THC distillate starts to condense and then immediately stopping the vacuum distilling, wherein said vacuum distilling removes residual solvent and volatile cannabidiol impurities from the clear Δ8-THC distillate; and (iv) Wiped film distilling the clear Δ8-THC distillate with a wiped film distillation unit to obtain a Δ8-THC oil having >99% Δ8-THC by HPLC, wherein said wiped film distilling removes high temperature cannabinoid impurities having a non-vacuum boiling higher than 180° C.

Figure 4:
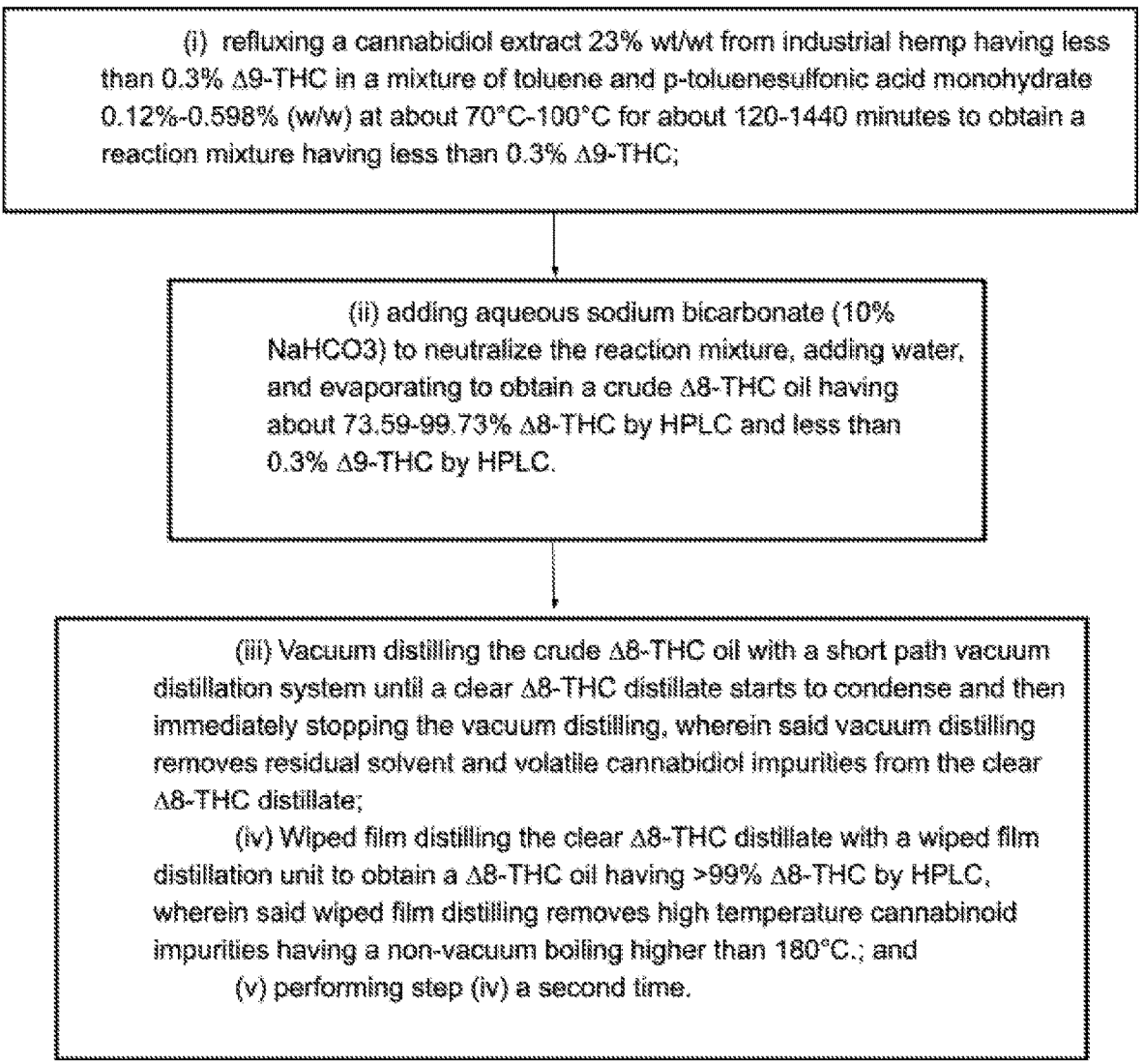
FIG. 4 is a process flowchart showing another preferred embodiment of the inventive process described and claimed herein for obtaining a crude Δ8-THC oil having about 73.59-99.73% Δ8-THC by HPLC and less than 0.3% Δ9-THC by HPLC and then performing vacuum distillation of the crude Δ8-THC oil with a short path vacuum distillation system to obtain a clear Δ8-THC distillate, followed by a wiped film distillation of the clear Δ8-THC distillate to obtain a Δ8-THC oil having >99% Δ8-THC by HPLC, followed by repeating the wiped film distillation a second time.
Figure 7:
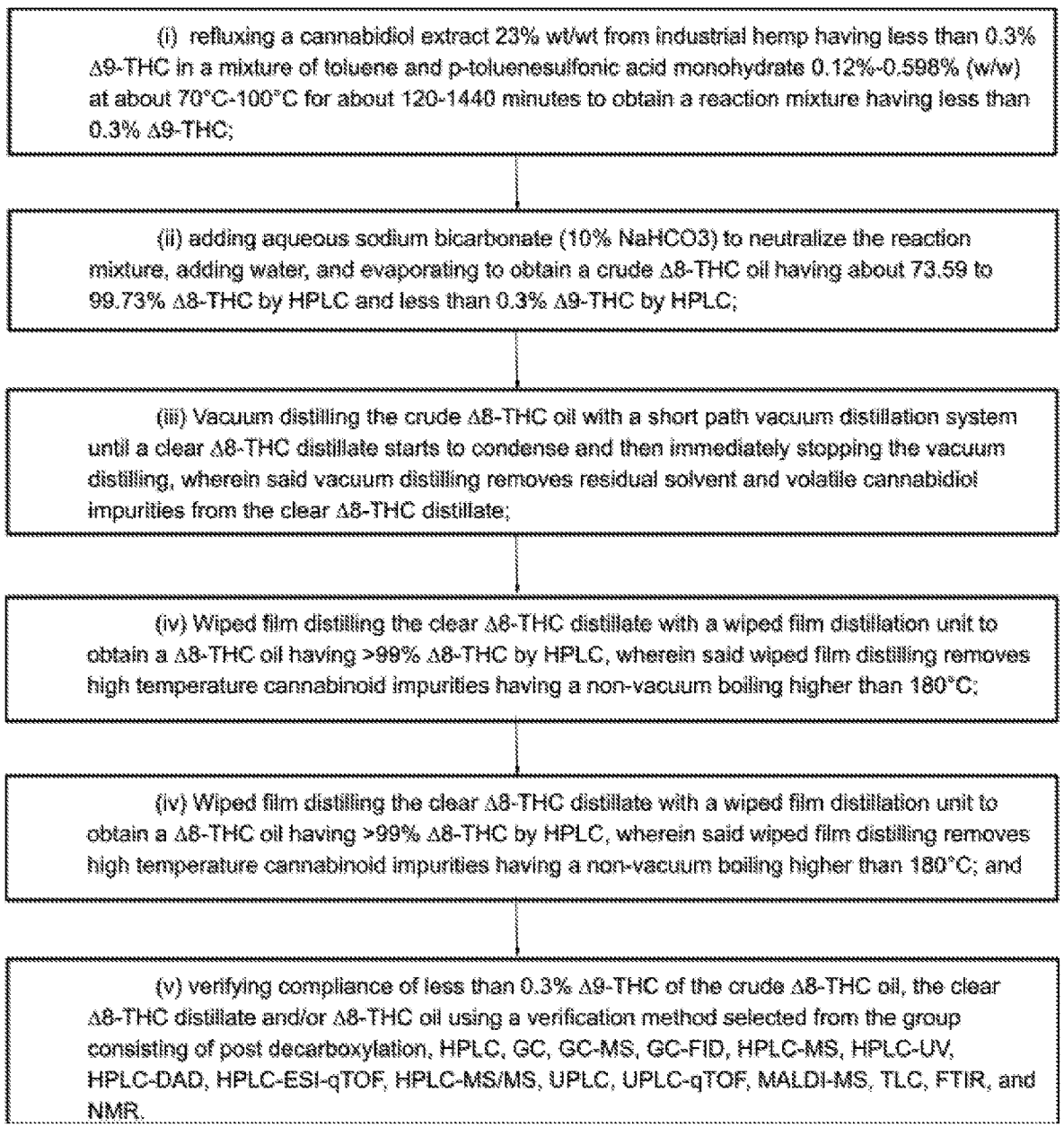
FIG. 7 is a process flowchart showing another preferred embodiment of the inventive process described and claimed herein for obtaining a crude Δ8-THC oil having about 73.59-99.73% Δ8-THC by HPLC and less than 0.3% Δ9-THC by HPLC, then performing vacuum distillation of the crude Δ8-THC oil with a short path vacuum distillation system to obtain a clear Δ8-THC distillate, followed by a wiped film distillation of the clear Δ8-THC distillate to obtain a Δ8-THC oil having >99% Δ8-THC by HPLC, optionally followed by repeating the wiped film distillation a second time, and verifying compliance of less than 0.3% Δ9-THC of the crude Δ8-THC oil, the clear Δ8-THC distillate and/or Δ8-THC oil using a verification method selected from the group consisting of post decarboxylation, HPLC, gas chromatography (GC), GC coupled with mass spectrometry (MS), GC coupled with flame ionization detection (FID), HPLC with MS, HPLC with ultraviolet (UV) absorbance, HPLC with diode array detection (DAD), HPLC-electrospray ionization-quadrupole time of flight (ESI-qTOF), HPLC-MS/MS, ultra-performance liquid chromatography (UPLC), UPLC-qTOF, matrix assisted laser desorption ionization mass spectrometry (MALDI-MS), thin layer chromatography (TLC), Fourier transform infrared spectroscopy (FTIR), and nuclear magnetic resonance spectrometry (NMR).

In another preferred embodiment, as shown in FIG. 4, the wiped film distilling is performed twice.

Any of the preferred embodiments herein may include wherein the source of cannabidiol extract is selected from the group consisting of CBD crude, CBD distillate, and CBD isolate, and wherein the mixture is refluxed at 70° C. for 120 minutes, the aqueous sodium bicarbonate is 10% NaHCO3, and the crude Δ8-THC oil is 91.68%-99.73% Δ8-THC by HPLC.

Any of the preferred embodiments herein may include wherein the mixture includes a second organic solvent selected from the group consisting of dichloromethane, dichloroethane, ethanol, cyclohexane, hexanes, heptanes, and a combination thereof, and wherein the mixture includes a second catalyst selected from the group consisting of Zinc Chloride, Hydrochloric acid, Sulfuric acid, Zinc Bromide, Boron Trifluoride, Boron Trifluoride Diethyl Etherate, and a combination thereof.

In a preferred embodiment, the invention includes a process of producing Δ8-tetrahydrocannabinol (Δ8-THC), comprising providing a source of Cannabidiol extract, adding a catalyst and organic solvent to create a reaction mixture, refluxing the reaction mixture for a specified time under acidic conditions, neutralizing the reaction, recovering a solvent product, and distilling the solvent product to obtain a crude Δ8-THC oil having >99% purity.

Any of the preferred embodiments herein may include a method wherein the refluxing is selected from the group consisting of a broad reflux performed for between 0.5 to about 48 hours, a medium range reflux performed for between 60 to 180 min, and a specific reflux performed for approximately 120 min., and wherein the resulting crude Δ8-THC oil is further purified using fractional, vacuum, short path, molecular, and/or wiped film distillation.

Any of the preferred embodiments herein may include wherein the dilution ratio of the Cannabinoid extract to the organic solvent is 3 to 6 on a weight basis.

Any of the preferred embodiments herein may include wherein the source Cannabidiol extract is CBD crude, CBD isolate or CBD distillate, wherein the organic solvent is toluene, wherein the catalyst is 2.6% of p-toluenesulfonic acid monohydrate, and wherein the refluxing is performed for between 60 to 180 minutes at a reaction temperature selected from the group consisting of a range between 50 to 100° C., a range between 60° C. to 80° C., and approximately 70° C.

Any of the preferred embodiments herein may include wherein the crude Δ8-THC having >99% purity is eluted with a second solvent or solvent mixture and separated from Δ9-THC on a Normal Phase HPLC column or a Reverse Phase HPLC column, following washing the column with the second solvent or solvent mixture, wherein the second solvent or solvent mixture is selected from toluene, ether in petroleum ether, and water-acetonitrile, wherein the eluting solvent or solvent mixture is the same as the washing solvent or solvent mixture.

Any of the preferred embodiments herein may include wherein the organic solvent consists essentially of dichloromethane, dichloroethane, ethanol, cyclohexane, hexanes, heptanes, toluene, and a combination thereof.

Any of the preferred embodiments herein may include wherein the catalyst is selected from the group consisting of Zinc Chloride or Hydrochloric acid or Sulfuric acid or Zinc Bromide or Boron Trifluoride or Boron Trifluoride Diethyl Etherate, p-toluenesulfonic acid monohydrate, and a combination thereof.

Any of the preferred embodiments herein may include wherein the acidic reaction mixture is neutralized using a quenching agent followed by addition of purified water, the quenching agent selected from the group consisting of sodium carbonate, sodium bicarbonate, sodium sulfate, sodium thiosulfate, a 10% NaHCO3 solution, and a combination thereof.

In another preferred embodiment, the invention provides a process, comprising: (i) dissolving 5 kg to 500 kg of CBD isolate with 25 to 250 liters of toluene to form a solution; (ii) loading the solution into a reaction vessel and heating; (iii) adding p-toluenesulfonic acid monohydrate (100 to 2 kg) to the reaction vessel and refluxing at 60-80° C. for 100-150 minutes; (iv) quenching the mixture with aqueous 10% NaHCO3, and then adding purified water; (v) evaporating the mixture to collect a crude oil having greater than 90% Δ8-THC; (vi) loading the crude oil into a short path vacuum distillation system having Raschig rings in a condensing head and heating to remove residual solvent and terpenes and obtain a clear distillate; (vii) loading the clear distillate into a wiped film distillation unit and collecting a distilled oil having greater than 99% Δ8-tetrahydrocannabinol (Δ8-THC).

Any of the preferred embodiments herein may include a pharmaceutical composition comprising the Δ8-THC made according to the processes herein and a pharmaceutically acceptable carrier, wherein the pharmaceutical composition is a topical formulation or a nutraceutical formulation.

Any of the preferred embodiments herein may include a process, comprising: dissolving a quantity of CBD isolate in toluene to form a solution; loading the solution into a reaction vessel and heating; adding p-toluenesulfonic acid monohydrate to the reaction vessel and refluxing at 60-80° C. for 100-150 minutes; quenching the mixture with aqueous 10% NaHCO3, and then adding purified water; evaporating the mixture to collect a crude oil having greater than 90% Δ8-THC; loading the crude oil into a short path vacuum distillation system having Raschig rings in a condensing head and heating to remove residual solvent and terpenes and obtain a clear distillate; loading the clear distillate into a wiped film distillation unit and collecting a distilled oil having greater than 99% Δ8-tetrahydrocannabinol (Δ8-THC).

Any of the preferred embodiments herein may include an organic solvent that comprises cyclohexane, ethanol, methanol, isopropanol, acetone, toluene, hexane, pentane, heptane, methylene chloride (dichloromethane), ethylene dichloride (dichloroethane), tetrahydrofuran, benzene, chloroform, purified water, diethyl ether, and/or xylene.

In a preferred embodiment, the organic solvent is toluene.

Any of the preferred embodiments herein may include catalyst that may be a Lewis and/or Bronsted Lowry acid comprising acetic acid, ascorbic acid, citric acid, hydrochloric acid, hydrogen chloride, phosphoric acid, sulfuric acid, p-toluenesulfonic acid, p-toluenesulfonic acid monohydrate, zinc chloride, zinc bromide, zinc iodide, tin chloride, tin bromide, tin iodide, magnesium chloride, magnesium bromide, magnesium iodide, silver chloride, silver bromide, silver iodide, boron trifluoride, or boron trifluoride diethyl etherate, In a preferred embodiment, the catalyst is p-toluenesulfonic acid monohydrate.

In some embodiments, the catalyst may be an activated powder comprising of activated carbon, bentonite clay, and/or bleaching clay.

In some embodiments, the reaction mixture is filtered before being loaded into the evaporation equipment by activated carbon, bentonite clay, bleaching clay, silica, diatomaceous earth, celite, and/or mag-sil.

In some embodiments, the reaction mixture is neutralized with cold water, another alkali metal hydrogen carbonate or a carbonate of an alkali metal.

In some embodiments the reaction mixture is stirred at room temp, stirred while being heated or stirred while being chilled.

In some embodiments Cannabidiol (CBD) isolate, distillate, crude can be used.

In some embodiments the reaction can be carried out under inert atmosphere with argon, nitrogen, and/or equivalent gas.

Any of the process embodiments herein may include a step of verifying compliance of less than 0.3% Δ9-THC of the crude Δ8-THC oil.

Any of the process embodiments herein may include a step of verifying compliance of less than 0.3% Δ9-THC of the crude Δ8-THC oil, and comprising another step of verifying compliance of less than 0.3% Δ9-THC of the clear Δ8-THC distillate and/or Δ8-THC oil.

Any of the embodiments herein may include a process for obtaining a crude Δ8-THC oil having about 73.59-99.73% Δ8-THC by HPLC and less than 0.3% Δ9-THC by HPLC, then performing vacuum distillation of the crude Δ8-THC oil with a short path vacuum distillation system to obtain a clear Δ8-THC distillate, followed by a wiped film distillation of the clear Δ8-THC distillate to obtain a Δ8-THC oil having >99% Δ8-THC by HPLC, optionally followed by repeating the wiped film distillation a second time, and including the step of verifying compliance of less than 0.3% Δ9-THC of the crude Δ8-THC oil, the clear Δ8-THC distillate and/or Δ8-THC oil using a verification method selected from the group consisting of post decarboxylation, HPLC, gas chromatography (GC), GC coupled with mass spectrometry (MS), GC coupled with flame ionization detection (FID), HPLC with MS, HPLC with ultraviolet (UV) absorbance, HPLC with diode array detection (DAD), HPLC-electrospray ionization-quadrupole time of flight (ESI-qTOF), HPLC-MS/MS, ultra-performance liquid chromatography (UPLC), UPLC-qTOF, matrix assisted laser desorption ionization mass spectrometry (MALDI-MS), thin layer chromatography (TLC), Fourier transform infrared spectroscopy (FTIR), and nuclear magnetic resonance spectrometry (NMR).

General Definitions

The embodiments herein and the various features and advantageous details thereof are explained more fully with reference to the non-limiting embodiments that are illustrated in the accompanying drawings and detailed description. Descriptions of well-known components and processing techniques are omitted so as to not unnecessarily obscure the embodiments herein. The examples used herein are intended merely to facilitate an understanding of ways in which the embodiments herein may be practiced and to further enable those of skill in the art to practice the embodiments herein. Accordingly, the examples should not be construed as limiting the scope of the embodiments herein.

Rather, these embodiments are provided so that this disclosure will be thorough and complete, and will fully convey the scope of the invention to those skilled in the art. Like numbers refer to like elements throughout. As used herein the term "and/or" includes any and all combinations of one or more of the associated listed items.

The terminology used herein is for the purpose of describing particular embodiments only and is not intended to limit the full scope of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof.

Unless defined otherwise, all technical and scientific terms used herein have the same meanings as commonly understood by one of ordinary skill in the art. Nothing in this disclosure is to be construed as an admission that the embodiments described in this disclosure are not entitled to antedate such disclosure by virtue of prior invention. As used in this document, the term "comprising" means "including, but not limited to."

Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, compositions or biological systems, which can, of course, vary. It is also to be understood that the terminology used herein is for the purpose of describing particular embodiments only, and is not intended to be limiting.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal subparts. As will be understood by one skilled in the art, a range includes each individual member.

Specific Definitions

The terms Delta-8-THC or Δ8-tetrahydrocannabinol or Δ8-THC refers to
6,6,9-trimethyl-3-pentyl-6a,7,10,10a-tetrahydrobenzo[c]chromen-1-ol (IUPAC 2019-06). Delta-8-THC can be represented by 2D structure as follows:

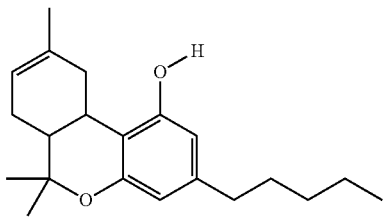 [SMILES: CCCCCc1cc(O)c2c(c1)OC(C)(C)C1CC=C(C)CC21]

The term delta-9-THC or Δ9-tetrahydrocannabinol or Δ9-THC refers to
(6aR,10aR)-6,6,9-trimethyl-3-pentyl-6a,7,8,10a-tetrahydrobenzo[c]chromen-1-ol (IUPAC 2019-06). Delta-9-THC can be represented by 2D structure as follows:

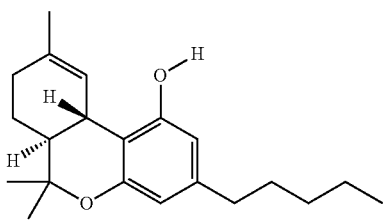

The term "pure" or "essentially pure" or "highly pure" refers to greater than 99% of Delta-8-THC in a given final product. Purity may be obtained using HPLC.

Figure 1:
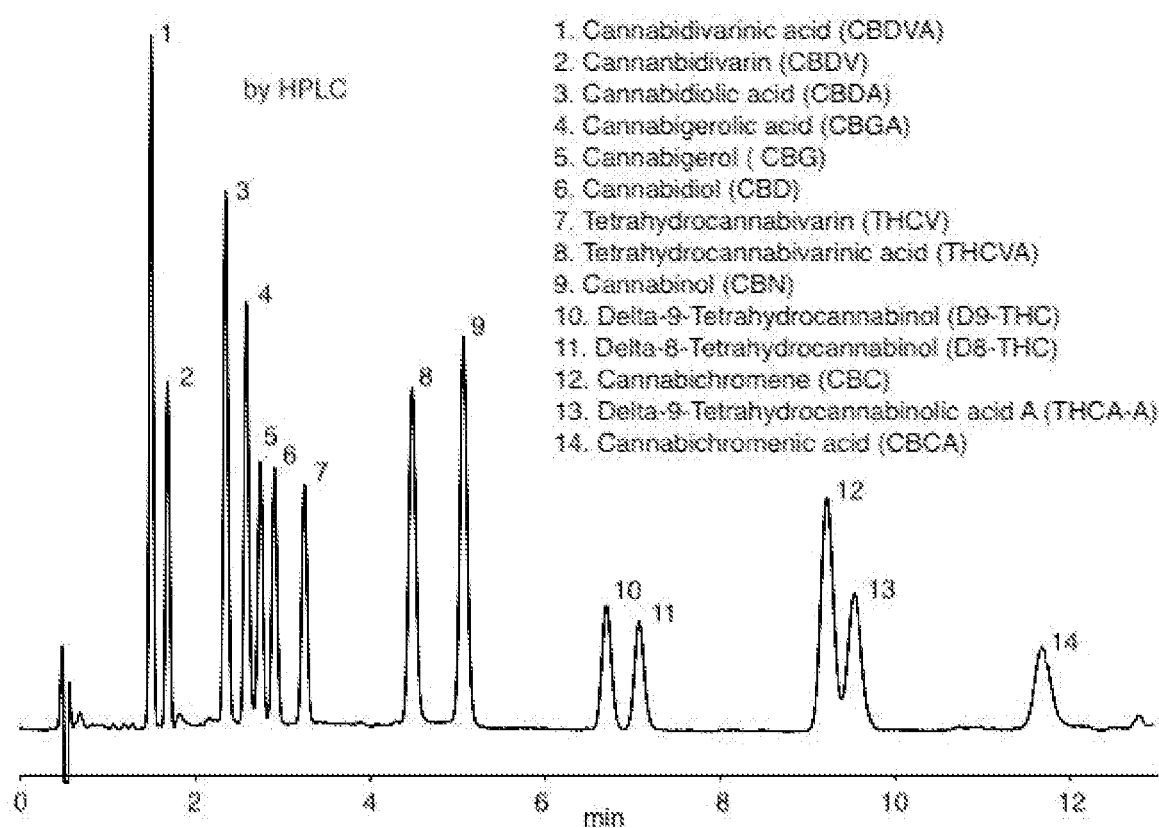
FIG. 1 is an HPLC graph showing the peaks of various cannabinoids.

FIG. 1 illustrates, using an HPLC chromatograph, the peaks of various cannabinoids. The first to come off at around 90 seconds is cannabidivarinic acid, followed by cannabidivarin at around 1'45". The next peaks, 3-4-5-6-7, fall between 2 minutes and 3 minutes (2'-3') are cannabidiolic acid, cannabigerolic acid, cannabigerol, cannabidiol, and tetrahydrocannabivarin, respectively. Between 4' and 5', the peaks for 8 and 9 are shown for tetrahydrocannabivarinic acid, and cannabidiol (CBD). Between 6' and 7', the peaks for 10 and 11 are Delta-9-tetrahydrocannabinol (D9-THC), and Delta-8-tetrahydrocannabinol (D8-THC). At around the 9 minute (9') mark the number 12 and 13 species are cannabichromene and Delta-9-tetrahydrocannabinolic acid A. Adn finally at about 11'30", the cannabichromenic acid comes off.

The term "CBD" refers to cannabidiol and has a molecular weight of 314.47 g/mol.

The term "CBD Distillate" refers to the process of applying high heat (boiling point) to raw extracted oil in a distillation chamber to separate the oil components and obtain highly pure CBD. CBD distillate does not contain or contains only a very small percentage of terpenes.

The term "CBD Isolate" refers to 99% pure CBD created by cooling and crystallizing CBD extract to form a white powder The term "hemp" does not include marijuana, and "natural hemp", "industrial hemp", or "hemp" as used herein refers to a variety of *Cannabis sativa* that contains less than 0.3% Delta-9-tetrahydrocannabinol (THC).

The term "cannabinoid" or "cannabinoids" as used herein encompasses at least the following substances: Δ-8 tetrahydrocannabinol, Δ-9-tetrahydrocannabinol (THC), cannabinol (CBN), cannabidiol (CBD), cannabigerol (CBG), Δ-9 (11)-tetrahydrocannabinol (exo-THC), cannabichromene (CBC), tetrahydrocannabinol-C3 (THC-C3), tetrahydrocannabinol/\(THC-C4).

Examples of Cannabinoids Include:

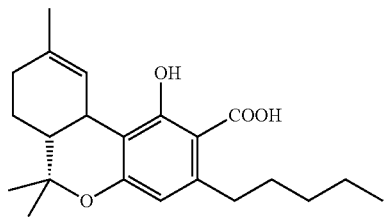

Tetrahydrocannabinolic acid
(THCA)

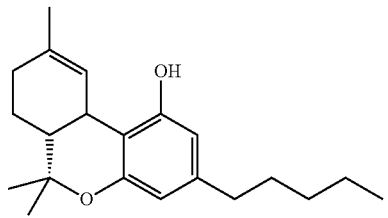

Tetrahydrocannabinol
(THC)

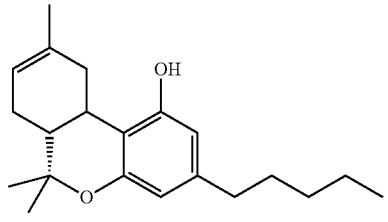

Delta-8-tetrahydrocannabinol
(Delta-8-THC)

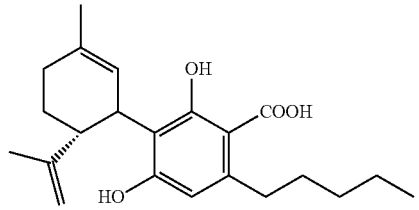

Cannabidiolic acid
(CBDA)

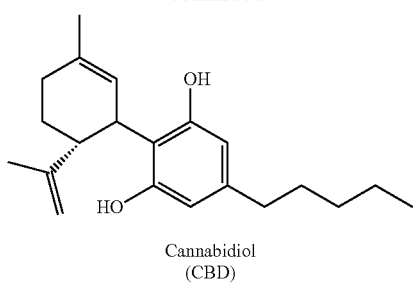

Cannabidiol
(CBD)

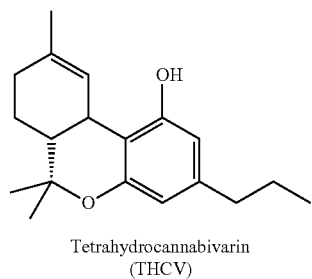

Tetrahydrocannabivarin
(THCV)

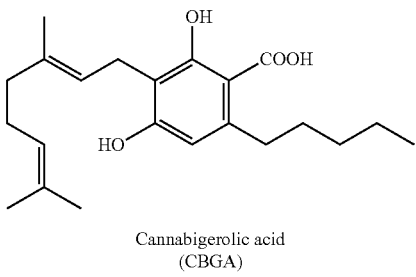

Cannabigerolic acid
(CBGA)

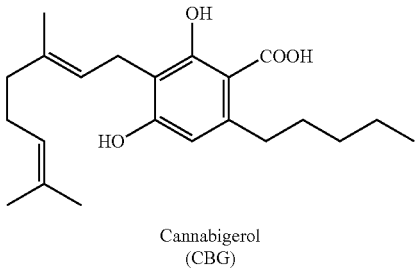

Cannabigerol
(CBG)

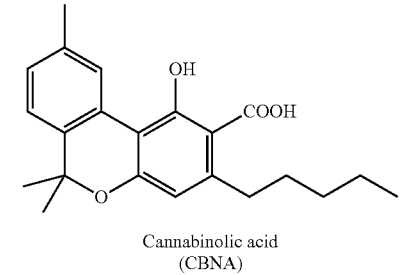

Cannabinolic acid
(CBNA)

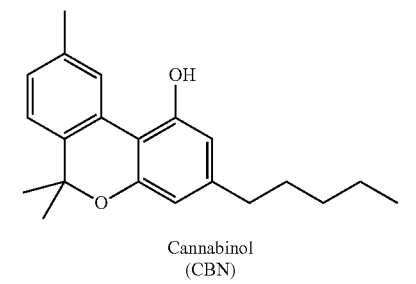

Cannabinol
(CBN)

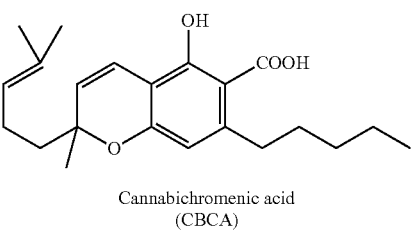

Cannabichromenic acid
(CBCA)

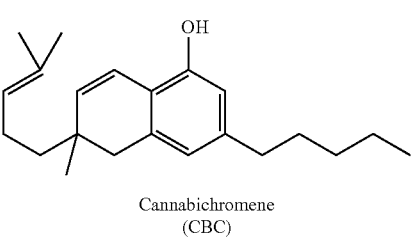

Cannabichromene
(CBC)

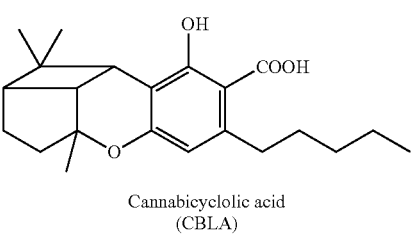

Cannabicyclolic acid
(CBLA)

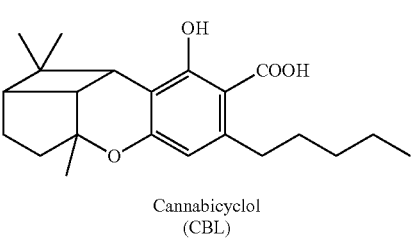

Cannabicyclol
(CBL)

Δ8-THC has a published boiling point at about 177° C. Δ9-THC has a published boiling point at about 157° C. Solvents, non-compliant cannabinoids, and volatile cannabinoids are defined as having a boiling point less than about 160° C. In distillation, as used herein, these low temperature compounds are known as "heads". High boiling point cannabinoids (vacuum) are defined herein as cannabinoids having a boiling point above about 180° C., and do not include, by definition Δ8-THC. In distillation, as used herein, these high temperature compounds are known as "tails", with the "main" being Δ8-THC, its crude oils, its distillates, and its purified oils.

Boiling points differ among cannabinoids. This permits separation by distillation techniques.

TABLE

Relevant cannabinoid structures and boiling points

| STRUCTURE | NAME | B.P. |
|---|---|---|
| | Δ-9-THC<br>Δ-9-thetrahydrocannabinol | 390.4° C. ± 42.0° C. at 760 mmHg;<br>157° C. under vacuum |
| | CBD cannabidiol | 463.9° C. ± 45.0° C. at 760 mmHg;<br>160-180° C. under vacuum |
| | Δ-8-THC<br>Δ-8-tetrahydricannabinol | 383.5° C. ± 42.0° C. at 760 mmHg;<br>175-178° C. under vacuum |

TABLE

Cannabinoid b.p. - lowest to highest, under vacuum

| NAME | B.P. ° C. |
|---|---|
| THCA | 105 |
| CBG | 105 |
| B-CARYOPHYLLENE | 119 |
| p-CYMENE | 134 |
| a-PINENE | 156 |
| D9-THC | 157 |
| CBD | 160-180 |
| B-MYRCENE | 166-168 |
| D8-THC | 175-178 |
| 1,8-CINEOLE | 176 |
| d-LIMONENE | 177 |
| CBC | 185 |
| CBN | 185 |
| LINALOOL | 198 |
| TERPINEOL-4-OL | 209 |
| a-TERPINEOL | 218 |
| THCV | 220 |
| PULEGONE | 224 |
| APIGENIN | 270 |
| QUERCETIN | 302 |
| CBDA | 316-531 |
| B-SITOSTEROL | 414 |

The term "extraction" refers to a process for obtaining raw Cannabinoid extract from dried Hemp plant material. Non-limiting illustrative processes include CO2 extraction, liquid chromatography, solvent extraction, and olive oil extraction. Extracts contain other plant components—major and minor cannabinoids, terpenes, and flavonoids—that isolates do not.

The term "CO2 extraction" refers to a process for obtaining CBD from industrial hemp that comprises by way of illustration in a non-limiting example the following steps:

—extraction with supercritical CO2 (e.g. 60° C., 250 bar);
—decarboxylation (e.g. 80° C., 2 hours); and—separation in a high pressure column (using CO2 as solvent). The method is shown to yield an extract containing CBD in approximately 90% purity.

The term "Winterization" refers to combining extracted CBD oil with ethanol and freezing overnight, which is then filtered to remove fats and other impurities, and the filtrate is heated to evaporate the ethanol.

The term "organic solvent" refers to ethanol, methanol, isopropanol, acetone, toluene, hexane, pentane, heptane, methylene chloride (dichloromethane), ethylene dichloride (dichloroethane), tetrahydrofuran, benzene, chloroform, purified water, diethyl ether, and/or xylene. In a preferred embodiment, the organic solvent is toluene.

The term "catalyst" refers to a Lewis and/or Bronsted Lowry acid comprising hydrochloric acid, hydrogen chloride, phosphoric acid, sulfuric acid, p-toluenesulfonic acid, p-toluenesulfonic acid monohydrate, zinc chloride, zinc bromide, zinc iodide, tin chloride, tin bromide, tin iodide, magnesium chloride, magnesium bromide, magnesium iodide, silver chloride, silver bromide, silver iodide, boron trifluoride, or boron trifluoride diethyl etherate, In a preferred embodiment, the catalyst is p-toluenesulfonic acid monohydrate.

The term "Short Path Distillation" refers to slowly heating CBD oil until extraneous substances having a different boiling point than CBD, such as heads (terpenes and high volatiles), and tails (high boiling point cannabinoids), are vaporized into a distillation tube, condensed by cooling coils, and separated, leaving purified CBD oil. Short Path distillation is generally not known for scalability into large batches. Short path distillation produces a high-quality distillate, but is limited in scale.

Short path distillation utilizes an apparatus with a multi-position receiver and condensing head. This process is very limited in scale and production, but can produce high-quality distillate with an experienced operator. Crude oil is heated in a boiling ask with a magnetic stirrer. The condensing head is jacketed and requires a recirculating chiller to cool the condensing head to condense the cannabinoid vapor back into a liquid form, with the different fractions condensing into different receiving flasks.

A short path will typically have 3 fractions—heads (terpenes and high volatiles), main body (THC/CBD), and tails (high boiling point cannabinoids).

The term "Thin Film Distillation" or "Wipe Film Distillation" refers to adding CBD crude oil, under vacuum, to the top of a heated vertical cylinder on a rotating plate. As the oil enters the cylinder (a jacketed, chilled condensing head), it encounters the rotating, specially designed wipers or rollers that create and renew a thin film on the heated surface. A long, condenser in the middle of the wipers in the evaporator body, cooled with recirculating fluid, condenses the vapor. Receiving vessels collect the distillate and the high temperature residue at the bottom. A recirculating heater maintains the temperature of the feed container and outer jacketed wiped film evaporator body. Refrigerated circulators cool the condenser and cold trap.

Optimizing the feed rate, vacuum, and temperatures is essential to yield the desired component composition in the distillate. This method reduces the exposure time of the oil. With a wiped film extraction, two passes through the system are required to achieve a distillate. As in distillation, wiped film strips the crude of low boiling point compounds first, for example, terpenes and leftover volatiles. Then, during the second pass, the residue is run again to achieve the final CBD distillate.

The term "hexanes" refers to mixed isomers of hexane used as a solvent. The boiling point of hexanes is 68-70 degrees Celsius.

The term "verification" or "compliance" refers to quantitative methods for ensuring a level of less than 0.3% Δ9-THC of the starting material, the reaction intermediates and reaction mixtures, the crude Δ8-THC oil, the clear Δ8-THC distillate, and the highly pure Δ8-THC oil.

Quantitative compliance verification methods contemplated as within the scope of the invention include, without limitation, a method selected from the group consisting of post decarboxylation, HPLC, gas chromatography (GC), GC coupled with mass spectrometry (MS), GC coupled with flame ionization detection (FID), HPLC with MS, HPLC with ultraviolet (UV) absorbance, HPLC with diode array detection (DAD), HPLC-electrospray ionization-quadrupole time of flight (ESI-qTOF), HPLC-MS/MS, ultra-performance liquid chromatography (UPLC), UPLC-qTOF, matrix assisted laser desorption ionization mass spectrometry (MALDI-MS), thin layer chromatography (TLC), Fourier transform infrared spectroscopy (FTIR), and nuclear magnetic resonance spectrometry (NMR).

EXAMPLES

The invention will now be described by means of examples, although the invention is not limited to these examples.

TABLE 1—Summary, Examples of Conversion of CBD to Δ8-THC

TABLE 1

Summary, Examples of Conversion of CBD to Δ8-THC
Summary of Examples

| | Solvent | Catalyst | Catalyst-to-solvent % | Time | Temp ° C. | Δ8 | Δ9 | CBD |
|---|---|---|---|---|---|---|---|---|
| Inventive Example 1 | Toluene | P-Tosic | 2.6 | 120 | 70 | 99.73 | N/D | N/D |
| Comparative Example 2 | Toluene | P-Tosic | 2.6 | 120 | 100 | 73.59 | N/D | N/D |
| Comparative Example 3 | Toluene | P-Tosic | 1 | 1440 | 100 | 87.01 | N/D | N/D |
| Comparative Example 4 | Toluene | P-Tosic | 1 | 2880 | 100 | 88.13 | 9.18 | N/D |
| Comparative Example 5 | Toluene | P-Tosic | 20 | 35 | 100 | 88.28 | 7.98 | N/D |
| Comparative Example 6 | Toluene | P-Tosic | 20 | 90 | 100 | 84.88 | 4.51 | N/D |
| Comparative Example 7 | Ethanol | P-Tosic | 3 | 120/30 | 30/60 | 3.20 | 2.49 | 89.43 |
| Comparative Example 8 | DCE | ZnCl2 | 250 | 1440 | 80 | 56.01 | 18.92 | N/D |
| Comparative Example 9 | DCE | ZnCl2 | 200 | 1440 | 80 | 62.13 | 30.55 | N/D |
| Comparative Example 10 | DCE | ZnCl2 | 200 | 720 | 80 | 14.36 | 27.73 | 40.41 |

Example 1—a Preferred Embodiment

CBD isolate (5000 g) was added and dissolved into toluene (25 L) to create a homogenized mixture. The solution was loaded into the reaction vessel and heat was added. P-toluenesulfonic acid monohydrate (130 g) was introduced to the reaction vessel. The mixture was refluxed at 70° C. for 120 minutes, although other time periods may be used, as discussed in alternative embodiments. The solution was then quenched with aqueous 10% NaHCO3, then with purified water, and evaporated. The collected crude oil showed the presence of 91.68% Δ8-THC by HPLC. This extract was then loaded into a distillation unit and purified through distillation. Raschig rings were used in the distillation heads to increase purity. The completed residue was clear and stable at room temperature. The collected distilled oil showed the presence of 99.73% Δ8-THC by HPLC. An example of an essentially pure Δ8-THC by HPLC is shown in FIG. 1

In example 1, CBD isolate may have a non-limiting molar mass of 314.47 g/mol with 5000 g equivalent to about 15.90 moles. Toluene may have a molar mass of 92.14 g/mol, and 25 liters of toluene at a density of 0.87 g/mL is about 21750 g, and is equivalent to about 236.05 moles. P-toluenesulfonic acid monohydrate has a molar mass of about 172.2 g/mol, and 130 g of p-tosic is equivalent to about 0.755 moles.

The Calculated Mass Fraction of CBD to Toluene to p-Tosic is:

5000 g+21750 g+130 g=26880 g, or 18.60%+80.92%+0.48%, respectively.

The calculated weight/weight ratios of grams solute in grams solvent is:

5000 g CBD isolate in 21750 g toluene=22.99 wt %
130 g p-tosic in 21750 g toluene=0.598 wt %
The Calculated Mole Fraction is:
15.9 mol CBD isolate/252.705 mol total=6.29% (mole fraction),
236.5 mol toluene/252.705 mol total=93.41% (mole fraction), and 0.755 mol p-tosic/252.705 mol total=0.299% (mole fraction).

Comparative Examples

Following are some comparative examples, i.e. failures, that show that only a variation of the process parameters will unexpectedly result in a failed product. Decreasing or increasing the % of the catalyst will change the amount of the Δ8-THC and the Δ9-THC in the final product. This is critical because anything above 0.3% Δ9-THC, by law, is a non-compliant product and must be destroyed. Similarly, changing the reflux time will change the amount of the Δ8-THC and the Δ9-THC in the final product. And changing the reflux temperature will change the amount of the Δ8-THC and the Δ9-THC in the final product. Further, performing a thermal distillation versus a vacuum short-path distillation will degrade various cannabinoids and result in higher impurities. And, letting the vacuum distillation run past the point where solvent and volatile, low boiling point cannabinoids are removed risks reducing yield of a Δ8-THC final product. Similarly, using only a single distillation process, e.g. without using the wiped film distillation, will leave high boiling point cannabinoids as impurities. As stated, these specific process parameters are critical because anything above 0.3% Δ9-THC, by law, is a non-compliant product and must be destroyed.

Δ8-THC Process Remaining Δ9-THC Compliant

It is important to note that the inventive process starts with an industrial hemp plant that is less than 0.3% Δ9-THC. The cannabidiol (CBD) extract obtained from the compliant hemp is processed to also have less than 0.3% Δ9-THC. The next step of processing with an organic acid, e.g. p-toluenesulfonic acid, in a chemically-related and compatible solvent, e.g. toluene, followed by quenching with a neutralizing compound, e.g. sodium bicarbonate, and washing with water, also yields a crude Δ8-THC oil having less than 0.3% Δ9-THC. Thus, the entire process stays Δ9-THC-compliant at each step. Further performing a short-path vacuum distillation to remove the low temperature impurities ensures that the crude Δ8-THC oil produces a Δ8-THC distillate without allowing the cannabidiol to isomerize to the unwanted and non-compliant Δ9-THC. Lastly, performing a wiped film distillation to remove the high temperature impurities also ensures that the Δ8-THC distillate produces a highly pure Δ8-THC oil having >99% Δ8-THC by HPLC without allowing any further isomerization to the unwanted and non-compliant Δ9-THC.

Example 2—Comparative Failure

CBD isolate (5000 g) was added and dissolved into toluene (25 L) to create a homogenized mixture. The solution was loaded into the reaction vessel and heat was added. P-toluenesulfonic acid monohydrate (130 g) was introduced to the reaction vessel. The mixture was refluxed at 100° C. for 120 minutes, although other time periods may be used, as discussed in alternative embodiments. The solution was then quenched with aqueous 10% NaHCO3, then with water, and evaporated. The collected crude oil showed the presence of 65.61% 48-THC by HPLC. This extract was then loaded into a distillation unit and purified through distillation. The completed residue was a light yellow color and stable at room temperature.

The collected distilled oil showed the presence of 73.59% Δ8-THC by HPLC.

Example 3—Comparative Failure

CBD isolate (5000 g) was added and dissolved into toluene (25 L) to create a homogenized mixture. The solution was loaded into the reaction vessel and heat was added. P-toluenesulfonic acid monohydrate (50 g) was introduced to the reaction vessel. The mixture was refluxed for 1440 minutes, although other time periods may be used, as discussed in alternative embodiments. The solution was then quenched with aqueous 10% NaHCO3, then with water, and evaporated. The collected crude oil showed the presence of 81.27% Δ8-THC by HPLC. This extract was then loaded into a distillation unit and purified through distillation.

The completed residue was clear and stable at room temperature. The collected distilled oil showed the presence of 87.01% Δ8-THC by HPLC.

Example 4—Comparative Failure

CBD isolate (5000 g) was added and dissolved into toluene (25 L) to create a homogenized mixture. The solution was loaded into the reaction vessel and heat was added. P-toluenesulfonic acid monohydrate (50 g) was introduced to the reaction vessel. The mixture was refluxed for 2880 minutes, although other time periods may be used, as discussed in alternative embodiments. The solution was then quenched with aqueous 10% NaHCO3, then with water, and evaporated. The collected crude oil showed the presence of 76.38% Δ8-THC but also had 5.26% Δ9-THC by HPLC. This extract was then loaded into a distillation unit and purified through distillation. The completed residue was clear and stable at room temperature. The collected distilled oil showed the presence of 88.13% Δ8-THC and 9.18% Δ9-THC by HPLC.

Example 5—Comparative Failure

CBD isolate (5000 g) was added and dissolved into toluene (25 L) to create a homogenized mixture. The solution was loaded into the reaction vessel and heat was added. P-toluenesulfonic acid monohydrate (1000 g) was introduced to the reaction vessel. The mixture was refluxed at 100° C. for 35 minutes, although other time periods may be used, as discussed in alternative embodiments. The solution was then quenched with aqueous 10% NaHCO3, then with water, and evaporated. The collected crude oil showed the presence of 79.31% Δ8-THC but also had 4.32% Δ9-THC by HPLC. This extract was then loaded into a distillation unit and purified through distillation. The completed residue was a light yellow color and stable at room temperature. The collected distilled oil showed the presence of 88.28% Δ8-THC and 7.98% Δ9-THC by HPLC.

Example 6—Comparative Failure

CBD isolate (5000 g) was added and dissolved into toluene (25 L) to create a homogenized mixture. The solution was loaded into the reaction vessel and heat was added. P-toluenesulfonic acid monohydrate (1000 g) was introduced to the reaction vessel. The mixture was refluxed at 100° C. for 90 minutes, although other time periods may be used, as discussed in alternative embodiments. The solution was then quenched with aqueous 10% NaHCO3, then with water, and evaporated. The collected crude oil showed the presence of 74.90% Δ8-THC but also had 2.92% Δ9-THC by HPLC. This extract was then loaded into a distillation unit and purified through distillation. The completed residue was a light yellow color and stable at room temperature. The collected distilled oil showed the presence of 84.88% Δ8-THC and 4.51% Δ9-THC by HPLC.

Example 7—Comparative Failure

CBD isolate (5000 g) was added and dissolved into ethanol (25 L) to create a homogenized mixture. The solution was loaded into the reaction vessel and heat was added. P-toluenesulfonic acid monohydrate (150 g) was introduced to the reaction vessel. The mixture was refluxed at 30° C. for 120 minutes, then refluxed at 60° C. for 30 minutes although other time periods may be used, as discussed in alternative embodiments. The solution was then quenched with aqueous 10% NaHCO3, then with water, and evaporated. The collected crude oil showed the presence of 2.92% Δ8-THC but also had 2.45% Δ9-THC and 85.87% CBD by HPLC. This extract was then loaded into a distillation unit and purified through distillation. The completed residue was a light yellow color and stable at room temperature. The collected distilled oil showed the presence of 3.20% Δ8-THC, 2.49% Δ9-THC, and 89.43% CBD by HPLC.

Example 8—Comparative Failure

CBD isolate (5000 g) was added and dissolved into dichloroethane (25 L) to create a homogenized mixture. The solution was loaded into the reaction vessel and heat was added. Zinc Chloride (12500 g) was introduced to the reaction vessel. The mixture was refluxed at 80° C. for 1440 minutes, although other time periods may be used, as discussed in alternative embodiments. The solution was then quenched with aqueous 10% NaHCO3, then with water, and evaporated. The collected crude oil showed the presence of 49.54% Δ8-THC but also had 15.25% Δ9-THC by HPLC. This extract was then loaded into a distillation unit and purified through distillation. The completed residue was a light yellow color and stable at room temperature. The collected distilled oil showed the presence of 56.01% Δ8-THC and 18.92% Δ9-THC by HPLC.

Example 9—Comparative Failure

CBD isolate (5000 g) was added and dissolved into dichloroethane (25 L) to create a homogenized mixture. The solution was loaded into the reaction vessel and heat was added. Zinc Chloride (10000 g) was introduced to the reaction vessel. The mixture was refluxed at 80° C. for 1440 minutes, although other time periods may be used, as discussed in alternative embodiments. The solution was then quenched with aqueous 10% NaHCO3, then with water, and evaporated. The collected crude oil showed the presence of 54.20% Δ8-THC but also had 25.93% Δ9-THC by HPLC. This extract was then loaded into a distillation unit and purified through distillation. The completed residue was a light yellow color and stable at room temperature. The collected distilled oil showed the presence of 62.13% Δ8-THC and 30.55% Δ9-THC by HPLC.

Example 10—Comparative Failure

CBD isolate (5000 g) was added and dissolved into dichloroethane (25 L) to create a homogenized mixture. The solution was loaded into the reaction vessel and heat was added. Zinc Chloride (10000 g) was introduced to the reaction vessel. The mixture was refluxed at 80° C. for 720 minutes, although other time periods may be used, as discussed in alternative embodiments. The solution was then quenched with aqueous 10% NaHCO3, then with water, and evaporated. The collected crude oil showed the presence of 12.20% Δ8-THC but also had 24.09% Δ9-THC and 37.84% CBD by HPLC. This extract was then loaded into a distillation unit and purified through distillation. The completed residue was a light yellow color and stable at room temperature. The collected distilled oil showed the presence of 14.36% Δ8-THC, 27.73% Δ9-THC, and 40.41% CBD by HPLC.

Example 11—Another Preferred Embodiment

CBD isolate (5000 g) was added and dissolved into toluene (25 L) to create a
homogenized mixture. The solution was loaded into the reaction vessel and heat was added.
P-toluenesulfonic acid monohydrate (130 g) was introduced to the reaction vessel. The mixture was refluxed at 70° C. for 120 minutes, although other time periods may be used, as discussed in alternative embodiments. The solution was then quenched with aqueous 10% NaHCO3, then with purified water, and evaporated. After the majority of the solvent has been evaporated, the collected crude oil showed the presence of 91.41% Δ8-THC by HPLC. The crude is then loaded into a short path vacuum distillation system. The temperature is adjusted until the residual solvent and terpenes are collected. Once the clear distillate starts to condense, the system is turned off, and the remaining crude is loaded into a wiped film distillation unit.

Parameters are set, and the material is run through the system in a much more efficient manner to establish the industrial scale processing desired by large manufacturers. Raschig rings were used in the short path distillation head to increase purity. The completed residue was clear and stable at room temperature. The collected distilled oil showed the presence of 99.68% Δ8-THC by HPLC.

Example 12—Another Preferred Embodiment

CBD isolate (50 kg) was added and dissolved into toluene (250 L) to create a
homogenized mixture. The solution was loaded into the reaction vessel and heat was added. P-toluenesulfonic acid monohydrate (1300 g) was introduced to the reaction vessel.

The mixture was refluxed at 70° C. for 120 minutes, although other time periods may be used, as discussed in alternative embodiments. The solution was then quenched with aqueous 10% NaHCO3, then with purified water, and evaporated. After the majority of the solvent has been evaporated, the collected crude oil showed the presence of greater than 90% Δ8-THC by HPLC. The crude is then loaded into a short path vacuum distillation system. The temperature is adjusted until the residual solvent and terpenes are collected. Once the clear distillate starts to condense, the system is turned off, and the remaining crude is loaded into a wiped film distillation unit. Parameters are set, and the material is run through the system in a much more efficient manner to establish the industrial scale processing desired by large manufacturers.

Raschig rings were used in the short path distillation head to increase purity. The completed residue was clear and stable at room temperature. The collected distilled oil showed the presence of greater than 99% Δ8-THC by HPLC.

Example 13—Compliance Verification Embodiment

Crude Δ8-THC oil having about 73.59-99.73% Δ8-THC by HPLC and less than 0.3% Δ9-THC by HPLC is obtained using a process described herein. Vacuum distillation of the crude Δ8-THC oil with a short path vacuum distillation system to obtain a clear Δ8-THC distillate is followed by a wiped film distillation of the clear Δ8-THC distillate to obtain a Δ8-THC oil having >99% Δ8-THC by HPLC, optionally followed by repeating the wiped film distillation a second time. The step of verifying compliance of less than 0.3% Δ9-THC of the crude Δ8-THC oil, the clear Δ8-THC distillate and/or Δ8-THC oil is performed at one or more points in the process using a verification method selected from the group consisting of post decarboxylation, HPLC, gas chromatography (GC), GC coupled with mass spectrometry (MS), GC coupled with flame ionization detection (FID), HPLC with MS, HPLC with ultraviolet (UV) absorbance, HPLC with diode array detection (DAD), HPLC-electrospray ionization-quadrupole time of flight (ESI-qTOF), HPLC-MS/MS, ultra-performance liquid chromatography (UPLC), UPLC-qTOF, matrix assisted laser desorption ionization mass spectrometry (MALDI-MS), thin layer chromatography (TLC), Fourier transform infrared spectroscopy (FTIR), and nuclear magnetic resonance spectrometry (NMR).

Pharmaceutical Compositions/Medicaments

Any of the compositions of the invention may be converted using customary methods into pharmaceutical compositions and medicaments. The pharmaceutical composition and medicaments contain the composition of the invention either alone or together with other active substances. Such pharmaceutical compositions and medicaments can be for oral, topical, rectal, parenteral, local, or inhalant use. They are therefore in solid or semisolid form, for example oils, drops, lotions, balm, pills, tablets, creams, gelatin capsules, capsules, suppositories, soft gelatin capsules, gels, foams, powders, and formulated for internal use. For parenteral uses, those forms for intramuscular or subcutaneous administration can be used, or forms for infusion or intravenous injection can be used, and can therefore be prepared as solutions of the compositions and medicaments or as powders of the active compositions to be mixed with one or more pharmaceutically acceptable excipients or diluents, suitable for the aforesaid uses and with an osmolarity that is compatible with the physiological fluids. For local use, those preparations in the form of creams or ointments for topical use or in the form of sprays may be considered; for inhalant uses, preparations in the form of sprays, for example nose sprays, may be considered. Preferably, the composition and medicaments is administered topically or orally.

Any of the pharmaceutical compositions and medicaments can be prepared by per se known methods for the preparation of pharmaceutically acceptable compositions which can be administered to patients, and such that an effective quantity of the active substance is combined in a mixture with a pharmaceutically acceptable vehicle. Suitable vehicles are described, for example, in Remington's Pharmaceutical Sciences (Nack Publishing Company, Easton, Pa., USA 1985).

On this basis, the pharmaceutical compositions and medicaments include, albeit not exclusively, the composition of the invention in association with one or more pharmaceutically acceptable vehicles or diluents, and are contained in buffered solutions with a suitable pH and iso-osmotic with the physiological fluids.

Any of the compositions and medicaments are indicated as therapeutic agents either alone or in conjunction with other therapeutic agents or other forms of treatment. For example, in the case of skin care or cosmetic use, or for nausea, anxiety, stress, chronic pain, acute pain and used as an appetite stimulant. The compositions and agents of the invention are intended for administration to humans or animals.

Example—Oral Formulation

A >99% pure D8-THC oil having less than 0.3% D9-THC is prepared, the D8-THC oil at a dosage of 5-14 mg/Kg/day is homogenized with a dietary oil, an optional secondary solvent and/or surfactant at 0.1-10% w/v, and an optional anti-oxidant. An optional sweetener or flavorant may be added. An oral formulation of pure D8-THC is obtained. The dietary oil may comprise medium chain (C8-C12) and long chain (C10-C22) dietary triglycerides selected from the group consisting of caprylic triglyceride, capric triglyceride, lauric triglyceride, myristic triglyceride, palmitic triglyceride, stearic triglyceride, oleic triglyceride, linoleic triglyceride, gamma linoleic triglyceride, ricinoleic triglyceride, arachidic triglyceride, behenic triglyceride, and derivatives and mixtures thereof. The dietary oil may also comprise, alone or in combination with MCT or LCT, sesame oil, vitamin E, soybean oil, vegetable oil, corn oil, olive oil, peanut oil, coconut oil, palmseed oil, and mixtures thereof. The optional secondary solvents are selected from ethanol, glycerol, propylene glycol, and polyethylene glycols.

Example—Oral Formulation

A >99% pure D8-THC oil having less than 0.3% D9-THC is prepared, the D8-THC oil at a dosage of 5-14 mg/Kg/day is formulated into a tincture, a gummi, or fast melt tab, by mixing a dietary wax, an optional secondary dietary oil, an optional secondary solvent and/or surfactant at 0.1-10% w/v, and an optional anti-oxidant. An optional sweetener or flavorant may be added. An oral formulation of pure D8-THC is obtained. The dietary wax may comprise bees wax, plant waxes, very long chain fatty acid waxes, and mixtures thereof. The dietary oil may comprise medium chain (C8-C12) and long chain (C10-C22) dietary triglycerides selected from the group consisting of caprylic triglyceride, capric triglyceride, lauric triglyceride, myristic triglyceride, palmitic triglyceride, stearic triglyceride, oleic triglyceride, linoleic triglyceride, gamma linoleic triglyceride, ricinoleic triglyceride, arachidic triglyceride, behenic triglyceride, and derivatives and mixtures thereof. The dietary oil may also comprise, alone or in combination with MCT or LCT, sesame oil, vitamin E, soybean oil, vegetable oil, corn oil, olive oil, peanut oil, coconut oil, palmseed oil, and mixtures thereof. The optional secondary solvents are selected from a very long chain fatty alcohol (C24-C34), ethanol, glycerol, propylene glycol, and polyethylene glycols.

Example—Oral Formulation

A >99% pure D8-THC oil having less than 0.3% D9-THC is prepared, the D8-THC oil at a dosage of 5-14 mg/Kg/day is formulated into a tincture, a gummi, or fast melt tab, by mixing with sesame oil and ethanol. An oral formulation of pure D8-THC is obtained.

Topical Formulations

In preferred embodiments, the present compositions can additionally comprise at least one skin conditioning agent. In this regard, the present compositions preferably contain about 1% to about 15% by weight, and more preferably from about 5% to about 10% of at least one agent. The skin conditioning agent can help provide the softening, smoothing, lubricating, and skin conditioning features of the presently preferred compositions.

Preferred non-limiting examples of skin conditioning agents useful in the present compositions include petrolatum, red petrolatum, white petrolatum, liquid petrolatum, semi-solid petrolatum, light mineral oil, heavy mineral oil, white mineral oil, mineral oil alcohols, calamine, derivatives thereof, and mixtures thereof Organosiloxane Any of the presently preferred compositions can further comprise at least one organosiloxane. Organosiloxanes useful in the present compositions can be volatile or nonvolatile, including but not limited to polyalkylsilicones, cyclic polyalkylsiloxanes, polydialkylsiloxanes, polydiarylsiloxanes, polyalkarylsiloxanes, or cyclomethicones.

Preferred polyalkylsiloxanes useful in this regard have a viscosity of from about 0.5 to about 100,000 centistokes at 25.degree. C., and more preferably have a viscosity of less than 500 centistokes at 25.degree. C.

Aqueous Solvent

Any of the present compositions additionally comprise an aqueous solvent. Preferably the aqueous solvent is present in the instant compositions from about 50% to about 95% by weight, and more preferably from about 60% to about 90% by weight.

Emollient

Certain of the presently preferred compositions can additionally comprise at least one emollient. The present compositions may contain about 0.01% to about 5% by weight, and more preferably from about 0.1% to about 1% by weight of an emollient.

Dermatologically Acceptable Excipients

Any of the preferred compositions discussed herein can additionally comprise at least one dermatologically acceptable excipient commonly known to those of ordinary skill in the art as useful in topical compositions. Preferred, non-limiting examples of dermatologically acceptable excipients useful in these compositions are those selected from the group consisting of moisturizers, preservatives, gelling agents, colorants or pigments, antioxidants, radical scavengers, emulsifiers, pH modifiers, chelating agents, penetration enhancers, derivatives thereof, and mixtures thereof Moisturizers Any of the presently preferred compositions may optionally further contain at least one moisturizer. Preferably, the presently preferred compositions can comprise about 0.01% to about 10% by weight of at least one moisturizer. Preferred non-limiting examples of moisturizers that can optionally be included in these compositions include glycerin, pentylene glycol, butylene glycol, polyethylene glycol, sodium pyrrolidone carboxylate, alpha-hydroxy acids, beta-hydroxy acids, polyhydric alcohols, ethoxylated and propoxylated polyols, polyols, polysaccharides, panthenol, hexylene glycol, propylene glycol, dipropylene glycol, sorbitol, derivatives thereof, and mixtures thereof Preservatives Any of the presently preferred compositions may optionally further contain at least one preservative. Preferred non-limiting examples of preservatives that can optionally be included in these compositions include benzyl alcohol, methyl paraben, ethyl paraben, derivatives thereof, and mixtures thereof. A particularly preferred preservative in this regard is benzyl alcohol or a derivative thereof. Additionally, the preservative is preferably present in an amount of about 0.1% to about 2.5% by weight of the overall weight of the composition.

Gelling Agents

Any of the presently preferred compositions may optionally further contain a gelling agent. Preferred non-limiting examples of gelling agents that can optionally be included in these compositions include various cellulose agents, such as cellulosic polymers, methylcellulose, hydroxyethylcellulose, hydroxypropylcellulose, and hydroxypropylmethylcellulose. Additional, non-limiting examples of gelling agents include gum arabic, gum tragacanth, locust bean gum, guar gum, xanthan gum, cellulose gum, sodium carbomer, carbomer, polyacrylic polymers, derivatives thereof, and mixtures thereof. Other suitable gelling agents which may be useful in the present compositions include aqueous gelling agents, such as neutral, anionic, and cationic polymers, derivatives thereof, and mixtures thereof. Exemplary polymers which may be useful in the preferred compositions in this regard include carboxy vinyl polymers, such as carboxypolymethylene. Additionally preferred gelling agents include Carbopol® and Carbomer® polymers (i.e. polyacrylic polymers) such as is available from Noveon Inc., Cleveland, Ohio. The gelling agent is preferably present in the instant compositions in an amount of from about 0.01% to about 10%, more preferably from about 0.1% to about 5%, and most preferably from about 0.1% to about 2%, by weight.

Anti-Oxidants

Any of the presently preferred compositions may optionally further contain at least one anti-oxidant. Preferably, the presently preferred compositions can comprise about 0.1% to about 5% by weight of at least one anti-oxidant. Preferred non-limiting examples of antioxidants that can optionally be included in these compositions include ascorbic acid, ascorbyl esters of fatty acids, magnesium ascorbyl phosphate, sodium ascorbyl phosphate, ascorbyl sorbate, tocopherol, tocopherol sorbate, tocopherol acetate, butylated hydroxy benzoic acid, thioglycolates, persulfate salts, 6-hydroxy-2,5,7,8-tetramethylchroman-2-carboxylic acid, lipoic acid, gallic acid, propyl gallate, uric acid, sorbic acid, lipoic acid, amines, N,N-diethylhydroxylamine, N-acetyl-L-cysteine, amino-guanidine, sulfhydryl compounds, glutathione, dihydroxy fumaric acid, lycine pidolate, arginine pilolate, nordihydroguaiaretic acid, bioflavonoids, curcumin, lysine, 1-methionine, proline, superoxide dismutase, silymarin, tea extracts, grape skin/seed extracts, melanin, rosemary extracts, derivatives thereof, and mixtures thereof.

Emulsifiers

Any of the presently preferred compositions may optionally further contain an emulsifier. Preferably, the presently preferred compositions can comprise about 0.05% to about 15% by weight, and more preferably from about 0.5% to about 10% by weight of at least one emulsifier. Preferred, non-limiting examples of specific emulsifiers useful in this regard include glycol esters, fatty acids, fatty alcohols, fatty acid glycol esters, fatty esters, fatty ethers, esters of glycerin, esters of propylene glycol, fatty acid esters of polyethylene glycol, fatty acid esters of polypropylene glycol, esters of sorbitol, esters of sorbitan anhydrides, carboxylic acid copolymers, esters and ethers of glucose, ethoxylated ethers, ethoxylated alcohols, alkyl phosphates, polyoxyethylene fatty ether phosphates, fatty acid amides, acyl lactylates, soaps, polyethylene glycol 20 sorbitan monolaurate (polysorbate 20), polyethylene glycol 5 soya sterol, steareth-2, steareth-20, steareth-21, ceteareth-20, PPG-2 methyl glucose ether distearate, ceteth-10, polysorbate 80, cetyl phosphate, potassium cetyl phosphate, diethanolamine cetyl phosphate, polysorbate 60, glyceryl stearate, PEG-8 stearate, PEG-100 stearate, derivatives thereof, and mixtures thereof.

pH Modifiers

Any of the presently preferred compositions may optionally further contain a pH modifier. Preferably, the presently preferred compositions can comprise about 0.001% to about 1% by weight of a pH modifier. Preferred non-limiting examples of neutralizing pH modifiers that can optionally be included in these compositions include inorganic hydroxides, inorganic oxides, inorganic salts of weak acids, derivatives thereof, and mixtures thereof. Preferred, non-limiting examples of inorganic hydroxides useful in this regard include ammonium hydroxide, alkali metal hydroxide, alkaline earth metal hydroxides, derivatives thereof, and mixtures thereof. Preferred inorganic hydroxides useful in this regard include ammonium hydroxide, monovalent alkali metal hydroxides such as sodium hydroxide and potassium hydroxide, divalent alkali earth metal hydroxides such as calcium hydroxide and magnesium hydroxide, derivatives thereof, and mixtures thereof. Preferred, non-limiting examples of inorganic oxides useful in this regard include magnesium oxide, calcium oxide, derivatives thereof, and mixtures thereof. Preferred, non-limiting examples of inorganic salts of weak acids useful in this regard include ammonium phosphate (dibasic), alkali metal salts of weak acids such as sodium acetate, sodium borate, sodium metaborate, sodium carbonate, sodium bicarbonate, sodium phosphate (tribasic), sodium phosphate (dibasic), potassium carbonate, potassium bicarbonate, potassium citrate, potassium acetate, potassium phosphate (dibasic), potassium phosphate (tribasic), alkaline earth metal salts of weak acids such as magnesium phosphate and calcium phosphate, derivatives thereof, and mixtures thereof.

Chelating Agents

Any of the presently preferred compositions may optionally further contain a chelating agent. Preferably, the presently preferred compositions can comprise about 0.01% to about 1% by weight of a chelating agent. Preferred non-limiting examples of chelating agents that can optionally be included in these compositions include citric acid, isopropyl (mono) citrate, stearyl citrate, lecithin citrate, gluconic acid, tartaric acid, oxalic acid, phosphoric acid, sodium tetrapyrophosphate, potassium monophosphate, sodium hexametaphosphate, calcium hexametaphosphate, sorbitol, glycine (aminoacetic acid), methyl glucamine, triethanolamine (trolamine), EDTA, DEG (dihydroxyethylglycine), DPTA (diethylene triamine pentaacetic acid), NTA (Nitrilotriacetic Acid), HEDTA (N-(hydroxyethyl)-ethylenetriaminetriacetic acid), aminocarboxylates, dimercaprol (BAL), larixinic acid (Maltol), unidentate ligands (fluoride and cyanide ions), diphenylthiocarbazone, 0-phenanthroline, barium diphenylamine sulfonate, sodium glucoheptonate, 8-hydroxyquinoline, olefin complexes (such as dicyclopentadienyl iron), porphyrins, phosphonates, pharmaceutically acceptable salts thereof, derivatives thereof, and mixtures thereof.

In addition to those enumerated above, any other pharmaceutically active agent, occlusive skin conditioning agent, emollient, penetration enhancer, organosiloxane, moisturizer, preservative, gelling agent, colorant or pigment, antioxidant, radical scavenger, emulsifier, pH modifier, chelating agent, or other dermatologically acceptable excipient commonly known to those of ordinary skill in the art as useful in topical compositions is contemplated as useful in the compositions described herein. Further, any non-toxic, inert, and effective topical carrier may be used to formulate the compositions described herein. Well-known carriers used to formulate other topical therapeutic compositions for administration to humans will be useful in these compositions. Examples of these components that are well known to those of skill in the art are described in The Merck Index, Thirteenth Edition, Budavari et al., Eds., Merck & Co., Inc., Rahway, N.J. (2001); the CTFA (Cosmetic, Toiletry, and Fragrance Association) International Cosmetic Ingredient Dictionary and Handbook, Tenth Edition (2004); and the "Inactive Ingredient Guide", U.S. Food and Drug Administration (FDA) Center for Drug Evaluation and Research (CDER) Office of Management, the contents of which are hereby incorporated by reference in their entirety. Examples of such useful pharmaceutically acceptable excipients, carriers and diluents include distilled water, physiological saline, Ringer's solution, dextrose solution, Hank's solution, and DMSO, which are among those preferred for use herein.

These additional other inactive components, as well as effective formulations and administration procedures, are well known in the art and are described in standard textbooks, such as Goodman and Gillman's: The Pharmacological Bases of Therapeutics, 8th Ed., Gilman et al. Eds. Pergamon Press (1990) and Remington's Pharmaceutical Sciences, 17th Ed., Mack Publishing Co., Easton, Pa. (1990), both of which are incorporated by reference herein in their entirety.

In another particularly preferred embodiment, the presently preferred pharmaceutical compositions are formulated in a lotion, cream, ointment, gel, suspension, emulsion, foam, aerosol, or other pharmaceutically acceptable topical dosage form.

Example—Topical Transdermal Composition

A >99% pure D8-THC oil having less than 0.3% D9-THC is prepared, the D8-THC oil at a dosage of 5-14 mg/Kg/day is formulated into a transdermal formulation by mixing pure D8-THC with a transdermal formulation base, the transdermal formulation base comprising an emulsion formed from an aqueous phase and an oil phase, and an penetration enhancer, an optional emulsifier, and an optional emollient. A topical transdermal D8-THC composition is thereby obtained.

Example—Topical Composition

A >99% pure D8-THC oil having less than 0.3% D9-THC is prepared, the D8-THC oil at a dosage of 5-14 mg/Kg/day is formulated as a cream, an ointment, foam, gel, lotion, ointment, paste, spray, or solution. A topical >99% pure D8-THC composition having less than 0.3% D9-THC is thereby obtained.

The cream or ointment is a water-in-oil or oil-in-water emulsion containing less than 20% water, greater than 50% hydrocarbons, waxes and/or polyols, and using a surfactant to create a semi-solid, spreadable composition. The foam is a cream or ointment packaged in a pressurized container and delivered with a gas.

Example—Topical Composition

A >99% pure D8-THC oil having less than 0.3% D9-THC is prepared, the D8-THC oil at a dosage of 5-14 mg/Kg/day is formulated as a topical composition comprising: (i) >99% pure D8-THC oil having less than 0.3% D9-THC, and (ii) a carrier formulation comprising: a self-emulsifying wax (i.e. glyceryl stearate, PEG-100 stearate), a polyol (glycerin), a fatty alcohol (cetyl alcohol), a moisturizer (allantoin), a hydrocarbon moisturizer/occlusive (petrolatum), an emulsifier (i.e. steareth-21), an antioxidant (tocopheryl acetate), and optionally a fragrance, a stabilizer (xanthan gum), a skin conditioner (i.e dipotassium glycyrrhizate), Aloe Barbadensis Leaf Juice, a surfactant (triethanolamine), an anti-inflammatory (i.e. bisabolol), and a preservative (disodium EDTA).

Any of the topical formulations herein may include a hydrocarbon base ("oleaginous"), such a white petrolatum or white ointment, an absorption base (water-in-oil) such as hydrophilic petrolatum or lanolin, water-removable base (oil-in-water) such as hydrophilic ointment, or a water-soluble base, such as polyethylene glycol ointment.

The topical formulation may also include a wax such as bees wax, plant waxes, very long chain fatty acid waxes, and mixtures thereof, an oil such as medium chain (C8-C12) and long chain (C10-C22) triglycerides, and alone or in combination with MCT or LCT, sesame oil, vitamin E, soybean oil, vegetable oil, corn oil, olive oil, peanut oil, coconut oil, palmseed oil, and mixtures thereof. Any of the topical formulations herein may include solvents are selected from a very long chain fatty alcohol (C24-C34), ethanol, glycerol, propylene glycol, and polyethylene glycols. Any of the topical formulations herein may include a penetration enhancer such as ethoxydiglycol (i.e. transcutol) or an equivalent.

Uses

As used herein, the terms "administering", "administration", and like terms refer to any method which, in sound medical or cosmetic practice, delivers the composition to a subject in such a manner as to provide a positive effect on a dermatological disorder, condition, or appearance. The compositions are preferably administered such that they cover the entire area to be treated. "Direct administration" refers to any method which, in sound medical or cosmetic practice, delivers the composition to a subject without the use of another composition, delivery agent, or device. "Indirect administration" refers to any method which, in sound medical or cosmetic practice, delivers the composition to a subject with the use of at least one other composition, delivery agent, or device.

As used herein, the phrases an "effective amount" or a "therapeutically effective amount" of an active agent or ingredient, or pharmaceutically active agent or ingredient, which are synonymous herein, refer to an amount of the pharmaceutically active agent sufficient enough to have a positive effect on the area of application. Accordingly, these amounts are sufficient to modify the skin disorder, condition, or appearance to be treated but low enough to avoid serious side effects, within the scope of sound medical or dermatological advice. A therapeutically effective amount of the pharmaceutically active agent will cause a substantial relief of symptoms when applied repeatedly over time. Effective amounts of the pharmaceutically active agent will vary with the particular condition or conditions being treated, the severity of the condition, the duration of the treatment, the specific components of the composition being used, and like factors.

EQUIVALENTS

Various of the above-disclosed and other features and functions, or alternatives thereof, may be combined into many other different systems or applications. Various presently unforeseen or unanticipated alternatives, modifications, variations or improvements therein may be subsequently made by those skilled in the art, each of which is also intended to be encompassed by the disclosed embodiments.

Having described embodiments for the invention herein, it is noted that modifications and variations can be made by persons skilled in the art in light of the above teachings. It is therefore to be understood that changes may be made in the particular embodiments of the invention disclosed which are within the scope and spirit of the invention as defined by the appended claims. Having thus described the invention with the details and particularity required by the patent laws, what is claimed and desired protected by Letters Patent is set forth in the appended claims.

The invention claimed is:

1. A process, comprising:
   (i) refluxing a cannabidiol extract from industrial hemp having less than 0.3% Δ9-tetrahydrocannabinol in a mixture of toluene and p-toluenesulfonic acid monohydrate at 70° C.-100° C. for 120-1440 minutes to obtain a reaction mixture having less than 0.3% Δ9-tetrahydrocannabinol;
   (ii) adding aqueous sodium bicarbonate to neutralize the reaction mixture, adding water, and evaporating to obtain a crude Δ8-tetrahydrocannabinol oil having 73.59-99.73% Δ8-tetrahydrocannabinol by high performance liquid chromatography and less than 0.3% Δ9-tetrahydrocannabinol by high performance liquid chromatography.

2. The process of claim 1, wherein the p-toluenesulfonic acid monohydrate is 0.12-0.598% (w/w) and the cannabidiol extract is 23% (wt/wt).

3. The process of claim 1, comprising
   (iii) Vacuum distilling the crude Δ8-tetrahydrocannabinol oil with a short path vacuum distillation system until a clear Δ8-tetrahydrocannabinol distillate starts to condense and then immediately stopping the vacuum distilling, wherein said vacuum distilling removes residual solvent and volatile cannabidiol impurities from the clear Δ8-tetrahydrocannabinol distillate; and
   (iv) Wiped film distilling the clear Δ8-tetrahydrocannabinol distillate with a wiped film distillation unit to obtain a Δ8-tetrahydrocannabinol oil having >99% Δ8-tetrahydrocannabinol by high performance liquid chromatography, wherein said wiped film distilling removes high temperature cannabinoid impurities having a non-vacuum boiling higher than 180° C.

4. The process of claim 3, comprising wherein the wiped film distilling is performed twice.

5. The process of claim 1, wherein the source of cannabidiol extract is selected from the group consisting of cannabidiol crude, cannabidiol distillate, and cannabidiol isolate, and wherein the mixture is refluxed at 70° C. for 120 minutes, the aqueous sodium bicarbonate is 10% NaHCO3, and the crude Δ8-tetrahydrocannabinol oil is 91.68%-99.73% Δ8-tetrahydrocannabinol by high performance liquid chromatography.

6. The method according to claim 1 wherein the mixture includes a second organic solvent selected from the group consisting of dichloromethane, dichloroethane, cyclohexane, ethanol, hexanes, heptanes, and a combination thereof, and wherein the mixture includes a second catalyst selected from the group consisting of Zinc Chloride, Hydrochloric acid, Sulfuric acid, Zinc Bromide, Boron Trifluoride, Boron Trifluoride Diethyl Etherate, and a combination thereof.

7. A process of producing Δ8-tetrahydrocannabinol, comprising providing a source of cannabidiol extract, adding a catalyst and organic solvent to create a reaction mixture, wherein the catalyst is selected from Zinc Chloride, Hydrochloric acid, Sulfuric acid, Zinc Bromide, Boron Trifluoride, Boron Trifluoride Diethyl Etherate, p-toluenesulfonic acid monohydrate, and a combination thereof, refluxing the reaction mixture for a specified time under acidic conditions, neutralizing the reaction, recovering a solvent product, and distilling the solvent product to obtain a crude Δ8-tetrahydrocannabinol oil having >99% purity,
  wherein the refluxing is selected from the group consisting of a broad reflux performed for between 0.5 to 48 hours, a medium range reflux performed for between 60 to 180 min, and a specific reflux performed for approximately 120 min, and wherein the resulting crude Δ8-tetrahydrocannabinol oil is further purified using fractional, vacuum, short path, molecular, and/or wiped film distillation,
  wherein the dilution ratio of the cannabidiol extract to the organic solvent is 3 to 6 on a weight basis wherein the source cannabidiol extract is cannabidiol crude, cannabidiol isolate or cannabidiol distillate, wherein the organic solvent is toluene, wherein the catalyst is 2.6% of p-toluenesulfonic acid monohydrate, and wherein the refluxing is performed for between 60 to 180 minutes at a reaction temperature selected from the group consisting of a range between 50° C. to 100° C., a range between 60° C. to 80° C., and approximately 70° C.

8. The method according to claim 7 wherein the crude Δ8-tetrahydrocannabinol having >99% purity is eluted with a second solvent or solvent mixture and separated from Δ9-tetrahydrocannabinol on a Normal Phase high performance liquid chromatography column or a Reverse Phase high performance liquid chromatography column, following washing the column with the second solvent or solvent mixture, wherein the second solvent or solvent mixture is selected from toluene, ether in petroleum ether, and water-acetonitrile, wherein the eluting solvent or solvent mixture is the same as the washing solvent or solvent mixture.

9. The method according to claim 7, wherein the organic solvent consists essentially of dichloromethane, dichloroethane, ethanol, cyclohexane, hexanes, heptanes, toluene, and a combination thereof.

10. The method according to claim 7, wherein the catalyst is p-toluenesulfonic acid monohydrate.

11. The method according to claim 7, wherein the acidic reaction mixture is neutralized using a quenching agent followed by addition of purified water, the quenching agent selected from the group consisting of sodium carbonate, sodium bicarbonate, sodium sulfate, sodium thiosulfate, a 10% NaHCO3 solution, and a combination thereof.

12. A process, comprising:
  dissolving 5 kg to 500 kg of cannabidiol isolate with 25 to 250 liters of toluene to form a solution;
  loading the solution into a reaction vessel and heating;
  adding p-toluenesulfonic acid monohydrate (1 kg to 2 kg) to the reaction vessel and refluxing at 60° C.-80° C. for 100-150 minutes;
  quenching the mixture with aqueous 10% NaHCO3, and then adding purified water;
  evaporating the mixture to collect a crude oil having greater than 90% Δ8-tetrahydrocannabinol;
  loading the crude oil into a short path vacuum distillation system having Raschig rings in a condensing head and heating to remove residual solvent and terpenes and obtain a clear distillate;
  loading the clear distillate into a wiped film distillation unit and collecting a distilled oil having greater than 99% Δ8-tetrahydrocannabinol.

13. The process of claim 1, comprising the step of verifying compliance of less than 0.3% Δ9-tetrahydrocannabinol of the crude Δ8-tetrahydrocannabinol oil using a verification method selected from the group consisting of post decarboxylation high performance liquid chromatography (HPLC), gas chromatography (GC), GC coupled with mass spectrometry (MS), GC coupled with flame ionization detection (FID), HPLC with MS, HPLC with ultraviolet (UV) absorbance, HPLC with diode array detection (DAD), HPLC-electrospray ionization-quadrupole time of flight (ESI-qTOF), HPLC-MS/MS, ultra-performance liquid chromatography (UPLC), UPLC-qTOF, matrix assisted laser desorption ionization mass spectrometry (MALDI-MS), thin layer chromatography (TLC), Fourier transform infrared spectroscopy (FTIR), and nuclear magnetic resonance spectrometry (NMR).

14. The process of claim 3, comprising the step verifying compliance of less than 0.3% Δ9-tetrahydrocannabinol of the crude Δ8-tetrahydrocannabinol oil, the clear Δ8-tetrahydrocannabinol distillate and/or Δ8-tetrahydrocannabinol oil using a verification method selected from the group consisting of post decarboxylation high performance liquid chromatography (HPLC) gas chromatography (GC), GC coupled with mass spectrometry (MS), GC coupled with flame ionization detection (FID), HPLC with MS, HPLC with ultraviolet (UV) absorbance, HPLC with diode array detection (DAD), HPLC-electrospray ionization-quadrupole time of flight (ESI-qTOF), HPLC-MS/MS, ultra-performance liquid chromatography (UPLC), UPLC-qTOF, matrix assisted laser desorption ionization mass spectrometry (MALDI-MS), thin layer chromatography (TLC), Fourier transform infrared spectroscopy (FTIR), and nuclear magnetic resonance spectrometry (NMR).

15. The process of claim 3, comprising the step verifying compliance of less than 0.3% Δ9-tetrahydrocannabinol of the crude Δ8-tetrahydrocannabinol oil, and comprising another step of verifying compliance of less than 0.3% Δ9-tetrahydrocannabinol of the clear Δ8-tetrahydrocannabinol distillate and/or Δ8-tetrahydrocannabinol oil.

16. The process of claim 15, wherein the verification method is selected from the group consisting of post decarboxylation, high performance liquid chromatography (HPLC), gas chromatography (GC), GC coupled with mass spectrometry (MS), GC coupled with flame ionization detection (FID), HPLC with MS, HPLC with ultraviolet (UV) absorbance, HPLC with diode array detection (DAD), HPLC-electrospray ionization-quadrupole time of flight (ESI-qTOF), HPLC-MS/MS, ultra-performance liquid chromatography (UPLC), UPLC-qTOF, matrix assisted laser desorption ionization mass spectrometry (MALDI-MS), thin layer chromatography (TLC), Fourier transform infrared spectroscopy (FTIR), and nuclear magnetic resonance spectrometry (NMR).

* * * * *